US011596586B2

(12) United States Patent
Guelakis et al.

(10) Patent No.: US 11,596,586 B2
(45) Date of Patent: Mar. 7, 2023

(54) PERSONAL CARE COMPOSITIONS WITH GLUTATHIONE PRECURSOR COMPRISING 4-SUBSTITUTED RESORCINOLS AND AMINO ACIDS

(71) Applicant: Conopco, Inc., Englewood Cliffs, NJ (US)

(72) Inventors: Marian Pereira Guelakis, Shelton, CT (US); Jianming Lee, Monroe, CT (US); Jose Guillermo Rosa, Cheshire, CT (US); Stephen Alan Madison, Newtown, CT (US); Tingyan Ml, Shanghai (CN); Anita Damodaran, Bangalore (IN); Annu Kumari, Keonjhar (IN); Nan Huang, Shanghai (CN); Bijan Harichian, Irvine, CA (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 17/589,569

(22) Filed: Jan. 31, 2022

(65) Prior Publication Data

US 2022/0211596 A1 Jul. 7, 2022

Related U.S. Application Data

(63) Continuation of application No. 16/470,425, filed as application No. PCT/CN2017/116999 on Dec. 18, 2017, now Pat. No. 11,260,005.

(30) Foreign Application Priority Data

Dec. 21, 2016 (WO) ................ PCT/CN2016/111293
Feb. 14, 2017 (EP) ..................................... 17156112

(51) Int. Cl.
| | |
|---|---|
| *A61Q 19/00* | (2006.01) |
| *A61K 8/34* | (2006.01) |
| *A61K 8/06* | (2006.01) |
| *A61K 8/44* | (2006.01) |
| *A61K 8/49* | (2006.01) |
| *A61Q 19/02* | (2006.01) |
| *A61Q 19/08* | (2006.01) |

(52) U.S. Cl.
CPC .............. *A61K 8/347* (2013.01); *A61K 8/064* (2013.01); *A61K 8/44* (2013.01); *A61K 8/442* (2013.01); *A61K 8/447* (2013.01); *A61K 8/4913* (2013.01); *A61K 8/4926* (2013.01); *A61Q 19/02* (2013.01); *A61Q 19/08* (2013.01)

(58) Field of Classification Search
CPC ........ A61Q 19/00; A61Q 19/08; A61Q 19/10; A61Q 19/02; A61K 2300/00; A61K 9/0014; A61K 8/347; A61K 8/064; A61K 8/44; A61K 8/442; A61K 8/4813; A61K 8/4926

USPC .......................................................... 424/60
See application file for complete search history.

(56) References Cited

U.S. PATENT DOCUMENTS

| | | | |
|---|---|---|---|
| 3,274,063 A | 9/1966 | Nieper et al. | |
| 3,786,076 A | 1/1974 | Morelle | |
| 3,819,825 A | 6/1974 | Goodwin | |
| 4,201,235 A | 5/1980 | Ciavatta | |
| 4,707,354 A | 11/1987 | Garlen et al. | |
| 4,801,579 A | 1/1989 | Rainer et al. | |
| 4,885,157 A | 12/1989 | Fiaschetti | |
| 5,133,958 A | 7/1992 | Stuckler | |
| 5,137,714 A | 8/1992 | Scott | |
| 5,198,465 A | 3/1993 | Dioguardi | |
| 5,254,331 A | 10/1993 | Mausner | |
| 5,416,075 A | 5/1995 | Carson | |
| 5,472,706 A | 12/1995 | Friedman et al. | |
| 5,582,817 A | 12/1996 | Otsu et al. | |
| 5,667,768 A | 9/1997 | Ramin | |
| 5,679,819 A | 10/1997 | Jones | |
| 5,887,747 A | 3/1999 | Burklin et al. | |
| 6,013,279 A | 1/2000 | Klett-Loch | |
| 6,149,925 A | 11/2000 | Mammone et al. | |
| RE37,934 E | 12/2002 | Hoffmann | |
| 6,592,908 B1 | 7/2003 | Crum | |
| 6,602,492 B2 | 8/2003 | Iwasaki et al. | |
| 6,858,217 B2 | 2/2005 | Kerschner et al. | |
| 6,863,897 B2 | 3/2005 | Love et al. | |
| 6,869,598 B2 | 3/2005 | Love et al. | |
| 6,992,062 B2 | 1/2006 | Usala | |

(Continued)

FOREIGN PATENT DOCUMENTS

| | | |
|---|---|---|
| CA | 2337772 | 1/2000 |
| CN | 101773458 | 7/2010 |

(Continued)

OTHER PUBLICATIONS

International Preliminary Report on Patentability in PCT/CN2017/116999; dated Apr. 26, 2019; World Intellectual Property Org. (WIPO).

(Continued)

*Primary Examiner* — Eisa B Elhilo
(74) *Attorney, Agent, or Firm* — Stephanie S. DelPonte

(57) ABSTRACT

Topical personal care compositions containing amino acids and 4-substituted resorcinols for potentiating glutathione synthesis within skin cells. The compositions can be used to improve skin appearance of chronological aging or photoaging, resulting from exposure to UV light/sunlight, or environmental pollutants. The compositions are also useful for attaining even skin color and reducing pigmentation, age spots and discoloration.

11 Claims, No Drawings

(56) References Cited

U.S. PATENT DOCUMENTS

| | | | |
|---|---|---|---|
| 7,105,570 | B2 | 9/2006 | Iwasaki et al. |
| RE39,734 | E | 7/2007 | Crum |
| 7,300,649 | B2 | 11/2007 | Tanojo et al. |
| 7,427,640 | B1 | 9/2008 | Katayama et al. |
| 7,740,831 | B2 | 6/2010 | Chiba et al. |
| RE42,645 | E | 8/2011 | Crum |
| 8,119,111 | B2 | 2/2012 | Malek |
| 8,241,681 | B2 | 8/2012 | Herrmann et al. |
| 8,299,127 | B2 | 10/2012 | Anjing et al. |
| 8,357,649 | B2 | 1/2013 | Chieffi et al. |
| 8,361,446 | B2 | 1/2013 | Muller et al. |
| 8,440,172 | B2 | 5/2013 | Johncock et al. |
| 8,722,026 | B2 | 5/2014 | Niki et al. |
| 8,735,442 | B2 | 5/2014 | Ashida et al. |
| 8,795,643 | B1 | 8/2014 | Anthony |
| 8,815,800 | B2 | 8/2014 | Pashkovski et al. |
| 8,865,143 | B2 | 10/2014 | Lu et al. |
| 10,751,267 | B2 | 8/2020 | Lou et al. |
| 10,980,718 | B2 | 4/2021 | Lou et al. |
| 11,077,039 | B2 | 8/2021 | Damodaran et al. |
| 11,337,908 | B2 | 5/2022 | Buchalova et al. |
| 2003/0194417 | A1 | 10/2003 | Iwasaki |
| 2005/0192229 | A1 | 9/2005 | Perricone |
| 2005/0271726 | A1 | 12/2005 | Crum |
| 2006/0063718 | A1 | 3/2006 | Perricone |
| 2006/0257351 | A1 | 11/2006 | Chiba |
| 2007/0213243 | A1 | 9/2007 | Yao et al. |
| 2008/0274068 | A1* | 11/2008 | Tanaka .............. A61K 8/498 424/60 |
| 2009/0263513 | A1 | 10/2009 | Marini |
| 2010/0305169 | A1 | 12/2010 | Robinson |
| 2010/0322876 | A1 | 12/2010 | Nguyen |
| 2011/0183040 | A1 | 7/2011 | Ermolin |
| 2011/0195103 | A1 | 8/2011 | Perez Arcas et al. |
| 2012/0034183 | A1 | 2/2012 | Cohen |
| 2012/0214871 | A1 | 8/2012 | Pehratovic et al. |
| 2013/0039871 | A1 | 2/2013 | Murata |
| 2013/0048567 | A1 | 2/2013 | Tongesayi |
| 2014/0065196 | A1 | 3/2014 | Gabbay |
| 2014/0162979 | A1 | 6/2014 | Palla-Venkata |
| 2015/0064122 | A1 | 3/2015 | Meyer et al. |
| 2015/0342854 | A1 | 12/2015 | Shibuya |
| 2016/0081902 | A1* | 3/2016 | Osborne ............. A61K 8/63 424/59 |
| 2016/0120782 | A1 | 5/2016 | Lee |
| 2016/0250241 | A1 | 9/2016 | Deren-Lewis |
| 2017/0079895 | A1 | 3/2017 | Edelson et al. |
| 2017/0112764 | A1 | 4/2017 | Wu |
| 2019/0328631 | A1 | 10/2019 | Lou et al. |
| 2020/0009034 | A1 | 1/2020 | Damodaran et al. |
| 2020/0016059 | A1 | 1/2020 | Guelakis |
| 2020/0108002 | A1 | 4/2020 | Damodaran et al. |
| 2020/0222293 | A1 | 7/2020 | Buchalova et al. |

FOREIGN PATENT DOCUMENTS

| | | |
|---|---|---|
| CN | 101797213 | 8/2010 |
| CN | 102150866 | 8/2011 |
| CN | 102366397 | 3/2012 |
| CN | 103442678 | 12/2013 |
| CN | 105147590 | 12/2015 |
| CN | 105919827 | 9/2016 |
| CN | 107411982 | 12/2017 |
| EP | 0815040 | 10/1996 |
| EP | 1269978 | 1/2003 |
| EP | 2572701 | 3/2013 |
| EP | 2921160 | 9/2015 |
| EP | 3103434 | 12/2016 |
| FR | 2608424 | 6/1988 |
| FR | 2660196 | 10/1991 |
| FR | 2997852 | 5/2014 |
| GB | 720561 | 12/1954 |
| GB | 874368 | 8/1961 |
| GB | 987800 | 3/1965 |
| GB | 1050756 | 12/1966 |
| GB | 2212722 | 8/1989 |
| JP | 61227515 | 10/1986 |
| JP | 5032533 | 2/1993 |
| JP | 6128143 | 5/1994 |
| JP | 2006001903 | 1/2006 |
| JP | 2009242321 | 10/2009 |
| JP | 2010280675 | 12/2010 |
| JP | 2014196275 | 10/2014 |
| JP | 2015030689 | 2/2015 |
| KR | 20160123753 | 10/2016 |
| WO | WO9505852 | 3/1995 |
| WO | WO9913819 | 3/1999 |
| WO | WO0003689 | 1/2000 |
| WO | WO0025740 | 5/2000 |
| WO | WO0069403 | 11/2000 |
| WO | WO03080011 | 10/2003 |
| WO | WO03105806 | 12/2003 |
| WO | WO2004082654 | 9/2004 |
| WO | WO2004103353 | 12/2004 |
| WO | WO2005097060 | 10/2005 |
| WO | WO2007021065 | 2/2007 |
| WO | WO2007070069 | 6/2007 |
| WO | WO2010090546 | 8/2010 |
| WO | WO2010113925 | 10/2010 |
| WO | WO2011155280 | 12/2011 |
| WO | WO2012002669 | 1/2012 |
| WO | WO2012094638 | 7/2012 |
| WO | WO2013044111 | 3/2013 |
| WO | WO201309250 | 6/2013 |
| WO | WO2015005563 | 1/2015 |
| WO | WO2016033183 | 3/2016 |

OTHER PUBLICATIONS

Search Report in EP17156112.9; dated Apr. 7, 2017, European Patent Office (EPO).

Search Report and Written Opinion in PCT/CN2017/116999; dated Mar. 13, 2018; World Intellectual Property Org. (WIPO).

Supplemental Search Report and Written Opinion in EP17883107.9; dated Dec. 11, 2019; European Patent Office (EPO).

International Preliminary Report on Patentability in PCT/CN2017/117006; dated Apr. 1, 2019; World Intellectual Property Org. (WIPO).

Search Report and Written Opinion in PCT/CN2017/117006; dated Mar. 14, 2018; World Intellectual Property Org. (WIPO).

Search Report and Written Opinion in EP17882397.7; dated Aug. 27, 2019; European Patent Office (EPO).

International Preliminary Report on Patentability in PCT/CN2017/117008; dated Apr. 22, 2019; World Intellectual Property Org. (WIPO).

Search Report and Written Opinion in PCT/CN2017/117008; dated Mar. 27, 2018; World Intellectual Property Org. (WIPO).

Search Report and Written Opinion in EP17882292.0; dated Jul. 23, 2020; European Patent Office (EPO).

Search Report & Written Opinion in EP17156128.5; dated Apr. 7, 2017; European Patent Office (EPO).

International Preliminary Report on Patentability in PCT/CN2017/117015; dated Apr. 26, 2019; World Intellectual Property Org. (WIPO).

Supplemental Search Report and Written Opinion in EP17885031.9; dated Nov. 11, 2019; European Patent Office (EPO).

Search Report and Written Opinion in PCT/CN2017/117015; dated Mar. 23, 2018; World Intellectual Property Org. (WIPO).

International Preliminary Report on Patentability in PCT/EP2017/083207; dated Mar. 1, 2019; World Intellectual Property Org. (WIPO).

Written Opinion in PCT/EP2017/083207; dated Dec. 20, 2018; World Intellectual Property Org. (WIPO).

Search Report and Written Opinion in PCT/EP2017/083207; dated Mar. 19, 2018; World Intellectual Property Org. (WIPO).

Written Opinion 2 in PCT/EP2017/083223; dated Jan. 15, 2019; World Intellectual Property Org. (WIPO).

Search Report and Written Opinion in PCT/EP2017/083223; dated Mar. 23, 2018; World Intellectual Property Org. (WIPO).

(56) References Cited

OTHER PUBLICATIONS

International Preliminary Report on Patentability in PCT/EP2017/083223; dated Apr. 3, 2019; World Intellectual Property Org. (WIPO).
Sigma-Aldrich Product Information for L-Cystine, Product No. C8755; Sigma-Aldrich, retrieved from www.sigma-alrdich.com, 1 page.
Quadro, Submicron Homogenizing, Quadro Engineering Corp., 2 pages (2016).
Chol, M., et al., "Glutathione precursors replenish decreased glutathione pool in cystinotic cell lines", Biochemical and Biophysical Research Communications, 324, pp. 231-235 (2004).
Constantinides, P. P., et al., "Enhanced intestinal absorption of an RGD peptide from water-in-oil microemulsions of different composition and particle size", Journal of Controlled Release, 34, pp. 109-116 (1995).
Dolphin, D., et al., "Glutathione: Chemical, biochemical and medical aspects", Cell Biochemistry & Function, 8(2), p. 139 (1990).
Kumano, Y., et al., "Studies of water-in-oil (w/o) emulsion stabilized with amino acids or their salts", Journal Society Cosmetic Chemists, 28(5), pp. 285-314 (1977).
Meister, A., et al., "Glutathione Metabolism and Its Selective Modification", The Journal of Biological Chemistry, 263(33), pp. 17205-17208 (1988).
Meister, A., et al., "Selective Modification of Glutathione Metabolism", Science, 220, pp. 471-477 (1985).
Tareen, N., et al., "The Effects of Short-Term Administration of a Novel Glutathione Precursor (FT061452) on Serum and Intracellular Glutathione Levels", ClinicalTrials.gov, 2 pages (2013) (available at: https://clinicaltrials.gov/ct2/show/NCT01251315?term=FT061452&draw=2&rank=1).
Tareen, N., et al., "The Effects of Short Term Adminstration of a Novel Glutathione Precursor (FTO61452)", RTRN Research Hub, 2 pages (2012).
Tyrrell, R. M., et al., "Correlation Between Endogenous Glutathione Content and Sensitivity of Cultured Human Skin Cells to Radiation at Defined Wavelenghts in the Solar Ultraviolet Range"; Photochemistry and Photobiology, 47(3), pp. 405-412 (1988).
Conditioner, Record ID 675306; Mintel GNPD; 2 pages (2007).
Frizz & Stray Hair Control Cream, Record ID541436; Mintel GNPD; 2 pages (2006).
Hydra-Filler Pro-Youth Boosting Moisturizer, Record ID 2117408; Mintel GNDP; 3 pages (2013).
Hydrating Mask, Record ID 2582251; Mintel GNPD; 3 pages (2014).
Hyal-Defence Hyaluronic Acid Protection Serum, Record ID 1850085; Mintel GNPD; 3 pages (2012).
Ja Yoon Cream, Record ID 4500777; Mintel GNPD; 6 pages (2016).
Mela BB Cream Pact IRF 35 SPF 50+/PA+++, Record ID 2740667; Mintel GNPD; 5 pages (2014).
Meso-Maks Anti-Wrinkle Lightening Mask, Record ID 2464407; Mintel GNPD; 4 pages (2014).
Molding Cream, Record ID 10204247; Mintel GNPD; 2 pages (2005).
Shape & Lift Volumising Gel, Record ID 680767; Mintel GNPD; 2 pages (2007).

\* cited by examiner

PERSONAL CARE COMPOSITIONS WITH GLUTATHIONE PRECURSOR COMPRISING 4-SUBSTITUTED RESORCINOLS AND AMINO ACIDS

FIELD OF THE INVENTION

The invention relates to topical personal care compositions containing ingredients which increase glutathione production within skin cells.

BACKGROUND OF THE INVENTION

Glutathione (GSH) is a tripeptide that consists of glutamate, cysteine, and glycine. It is present in all mammalian tissues. It is the main anti-oxidant in the living body: it protects cells from oxidation by quenching reactive oxygen species. GSH is believed to play a significant role in protecting cells against the cytotoxic effects of ionizing radiation, heat, certain chemicals, and significantly, solar UV radiation (Tyrell et al., Photochem. Photobiol. 47: 405-412, 1988; Meister, J. Biol. Chem. 263: 205-217, 1988; Meister, Science 200:471-477, 1985). While true in all areas of the body, this is particularly important in the skin, which is so greatly exposed to the damaging effects of radiation, particularly UV radiation, and environmental pollutants. Decrease in the intracellular concentration of glutathione in skin is associated with cell damage, inflammation, skin darkening, discoloration, spots or freckles caused by exposure to ultraviolet radiation, physiological aging, and the like. It is, therefore, highly desirable to enhance the generation of glutathione in skin.

A logical approach would seem to be to provide cells with an exogenous source of GSH (e.g. through ingestion or topical delivery). Unfortunately, GSH is not bioavailable when administered exogenously, i.e. where localized extracellularly, it is broken down into its constituent amino acids (glutamate, cysteine, and glycine) for cellular uptake and synthesis of the GSH tripeptide. Thus, GSH is not directly transported into the cells and therefore does not itself result in an intracellular increase of glutathione. Biosynthesis of GSH occurs in the cell in a tightly regulated manner. The quantity of glutathione in cells depends to a large degree on the availability of cysteine in the cells. Cysteine, a composite amino acid of GSH, may increase cellular levels of GSH, but exposed sulfhydryl group of cysteine renders it unstable and reactive and also causes strong unpleasant odor. Unlike cysteine, cystine can be administered safely; cystine is transported into the cell and converted to cysteine within the cell, the cysteine then being available for intracellular GSH production.

Topical compositions containing various amino acids and other skin care actives have been described, see e.g. Tanojo U.S. Pat. No. 7,300,649B, Laboratoire Filorga product, Schlachter WO 00/03689, Ermolin et al. US2011183040, Garlen et al. U.S. Pat. No. 4,707,354, Muller et al. U.S. Pat. No. 8,361,446, Hermann et al. U.S. Pat. No. 8,241,681. Compositions for potentiating intracellular glutathione production have been described. See e.g. Chiba et al. U.S. Pat. No. 7,740,831, Crum et al (USRE37934, USRE42645, WO2016/033183, and US20050271726); Mammone U.S. Pat. No. 6,149,925, and Perricone US 20060063718.

Cystine is normally derived from the diet. Delivery of cystine from topical compositions, however, is challenging due to its extremely low solubility in biologically acceptable vehicle in a neutral pH range, which is the pH range required for topical application. The solubility of cystine in water is 0.112 mg/ml at 25° C.; cystine is more soluble in aqueous solutions with pH less than 2 or pH above 8.

The present invention is based in part on a surprising finding that a combination of cystine with a specific class of resorcinols achieves a synergistic increase in intracellular glutathione levels, thus counter-acting the drawback of cystine's low solubility at neutral pH. Furthermore, by virtue of including the resorcinol, only 2 out of the 3 amino acids are sufficient to attain synergistic increase in intracellular production of glutathione.

SUMMARY OF THE INVENTION

In one embodiment, a personal care composition according to the invention comprises:
a. glutathione precursor comprising, by weight of the composition:
   i. from about 0.001% to about 2% of cystine;
   ii. from about 0.01 to about 10% of a glutamate source; and
   iii. from about 0.001 to about 3% of a resorcinol of Formula I:

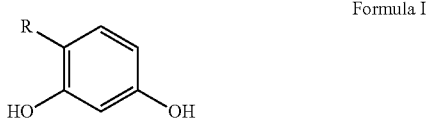

wherein R is an ethyl group optionally substituted with a phenyl or substituted phenyl group or a straight or branched C3 to C16 alkyl group optionally substituted with a phenyl group or substituted phenyl group; and
b. a cosmetically acceptable carrier;
c. wherein the pH of the composition is in the range of from about 3.5 to about 8.5.

In one embodiment, the topical cosmetic skin composition is a leave-on composition, especially a leave-on non-solid composition.

In one embodiment, the present invention provides a method of improving skin appearance, comprising applying the personal care composition to the skin.

In one embodiment, the present invention provides a method of attaining even skin color and reducing pigmentation, age spots and discoloration, comprising applying the composition to skin.

The compositions of the invention enhance the synthesis of glutathione in skin cells, and therefore, can be used to improve skin appearance of chronological aging or photoaging, resulting from exposure to UV light/sunlight, or environmental pollutants. A preferred method of obtaining the benefits of the composition is via regular/chronic topical application of the composition, to prevent development of skin damage which may result from even routine exposure to UV light or other environmental insults which generate reactive oxygen species.

DETAILED DESCRIPTION OF THE INVENTION

Throughout the specification and claims, the following terms take the meanings explicitly associated herein, unless the context clearly dictates otherwise.

The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention. In addition, each of the examples given in connection with the various embodiments of the invention which are intended to be illustrative, and not restrictive.

Except in the examples, or where otherwise explicitly indicated, all numbers in this description indicating amounts of material or conditions of reaction, physical properties of materials and/or use are to be understood as modified by the word "about." All amounts are by weight of the final composition, unless otherwise specified. The disclosure of the invention as found herein is to be considered to cover all embodiments as found in the claims as being multiply dependent upon each other irrespective of the fact that claims may be found without multiple dependency or redundancy. In specifying any range of concentration or amount, any particular upper concentration can be associated with any particular lower concentration or amount.

"Comprising" is intended to mean "including" but not necessarily "consisting of" or "composed of." In other words, the listed steps or options need not be exhaustive.

"Skin" is meant to include skin on the face, neck, chest, back, arms (including underarms), hands, legs, buttocks and scalp.

"Leave-on composition" refers to a composition that is applied to the skin and is not intended to be washed or rinsed off for some period of time, specifically hours, as contrasted with skin cleansing or wash-off or rinse-off compositions which are rinsed off or washed off immediately or minutes after the application.

"Non-solid" with respect to the composition means that the composition has a measurable viscosity (measurable for instance with a Brookfield Viscometer DV-I+ (20 RPM, RV6, 30 Seconds, 20° C.) in the range of from 1 Pas to 500 Pas, preferably from 2 Pas to 100 Pas, more preferably from 3 Pas to 50 Pas.

"Personal care composition" refers to any product applied to a human body for improving appearance, sun protection, cleansing, odor control, moisturization or general aesthetics. Non-limiting examples of personal care compositions include skin lotions, creams, gels, lotions, facial masks, sticks, shampoos, conditioners, shower gels, toilet bars, antiperspirants, deodorants, shave creams, depilatories, lipsticks, foundations, mascara, sunless tanners and sunscreen lotions.

"Skin cosmetic composition" refers to any product applied to a human body for improving appearance, sun protection, reducing wrinkled appearance or other signs of photoaging, odor control, skin lightening, even skin tone, or general aesthetics. Non-limiting examples of topical cosmetic skin compositions include skin lotions, creams, facial masks, gels, sticks, antiperspirants, deodorants, lipsticks, foundations, mascara, liquid or gel body washes, soap bars, sunless tanners and sunscreen lotions.

Personal care composition of the present technology is preferably a leave-on non-solid skin cosmetic composition, because such compositions are the most challenging in terms of incorporating cystine due to its low solubility.

Glutathione ("GSH") Precursor

The GSH precursor according to the present invention comprises amino acids (glutamate and cystine and, optionally, glycine) and a 4-substituted resorcinol. In one embodiment, the amino acids in the GSH precursor are cystine and glutamate source. In one embodiment, the amino acids in the GSH precursor are cystine and glutamate source and glycine.

Amino acids included in the inventive composition are present as L stereo isomers, since this is the most abundant and natural isomeric form found in nature. Since the building blocks of naturally-occurring proteins found in human skin, hair and nails are amino acids with the L isomeric form, it is expected that L stereo isomer amino acids contained within personal care products of the present invention can have a greater interaction with these proteins that is intrinsically more biocompatible in nature compared to the D stereo isomeric form. In addition, commercial production and supply of L stereo isomer amino acids is significantly higher compared to the D stereo isomeric form. Finally, L stereo isomer amino acids are also more cost effective to produce, more sustainable, more eco-friendly and available at a lower cost compared to D stereo isomer amino acids.

Any of the amino acids included in the present invention may be in the form of a salt, ester, or a salt thereof and the term "cystine," "glutamate source", and "glycine" used in the present specification also encompasses salts, esters, and salts of such esters. The salt, ester, and salt of such ester is not particularly limited as long as it is acceptable for topical application. For example, salts with inorganic acid or organic acid or anionic surfactants can be mentioned. As the inorganic acid, for example, hydrochloric acid, hydrobromic acid, nitric acid, sulfuric acid, phosphoric acid and the like can be mentioned, and as the organic acid C1-C18 linear, branched or cyclic, saturated or unsaturated, unsubstituted or substituted with heteroatoms, for example formic acid, acetic acid, trifluoroacetic acid, propionic acid, lactic acid, tartaric acid, oxalic acid, fumaric acid, succinic acid, maleic acid, citric acid, malonic acid, methanesulfonic acid, stearic acid, oleic acid, 12-hydroxystearic acid, ricinoleic acid, and the like can be mentioned.

As the salt with a base, for example, alkali metal salts such as sodium salt, potassium salt and the like, alkaline earth metal salts such as calcium salt, magnesium salt and the like, and the like can be mentioned.

Esters of amino acids are typically $C_1$-$C_8$ esters or salts thereof, or in the alternative $C_1$-$C_5$ esters, or in the alternative $C_1$-$C_3$ esters. Such esters may be straight or branched or cyclic. Especially esters of cystine are beneficial, due to their increased solubility, compared to cystine. Methyl and ethyl esters of cystine or salts thereof are most preferred, due to their efficacy to boost glutathione production and provide antioxidant activity. When salts of esters are used, the same salts are suitable as listed above.

Glutamate source can be present in the form of its functional equivalents—glutamine, glutamic acid and/or pyroglutamic acid and/or their salts may be employed. Pyroglutamic acid (and/or salts thereof) is preferred since it is more stable than glutamine or glutamic acid. In one embodiment, amino acids in GSH precursor are cystine and pyroglutamic acid (and/or salts thereof). In one embodiment, amino acids in GSH precursor are cystine and pyroglutamic acid and glycine (and/or salts thereof).

4-substituted Resorcinol of Formula I

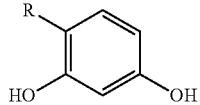

(Formula I)

wherein R is an ethyl group optionally substituted with a phenyl or substituted phenyl group or C3 to C16 straight or branched alkyl group optionally substituted with a phenyl or substituted phenyl group, is a component of GSH precursor included in the invention. It has been found that by virtue of including amino acids and resorcinol described herein glutathione production is synergistically increased, thus overcoming the drawback of cystine's limited solubility. Furthermore, by virtue of including the resorcinol, only 2 out of the 3 amino acids are sufficient to attain synergistic increase in intracellular production of glutathione.

Resorcinol derivatives of formula (I) are preferably the compounds selected from the group consisting of 4-ethylresorcinol, 4-propylresorcinol, 4-isopropylresorcinol, 4-butylresorcinol, 4-pentylresorcinol, 4-hexylresorcinol, 4-heptylresorcinol, 4-octyl resorcinol, 4-nonylresorcinol, 4-decylresorcinol, 4-dodecylresorcinol, 4-(1-methylpropyl)resorcinol, 4-(1-ethylpropyl)resorcinol, 4-(1-phenylethyl)resorcinol, 4-(2-phenylethyl)resorcinol, 4-(1-phenylpropyl)resorcinol, 4-(2-phenyl propyl) resorcinol, 4-(3-phenylpropyl) resorcinol, 4-(1-phenylbutyl)resorcinol, 4-(2-phenylbutyl)resorcinol, 4-(3-phenylbutyl)resorcinol, 4-(4-phenylbutyl)resorcinol, 4-(1-phenylhexyl)resorcinol, 4-(2-phenylhexyl)resorcinol, 4-[1-(2-methylphenyl)ethyl]resorcinol, 4-[1-(3-methylphenyl)ethyl]resorcinol, 4-[1-(4-methylpheny)ethyl]resorcinol, 4-[2-(2-methylphenyl)ethyl]resorcinol, 4-[2-(3-methylphenyl)ethyl]resorcinol, 4-[2-(4-methylphenyl)ethyl]resorcinol, 4-[1-(4-methylphenyl)propyl]resorcinol, 4-[1-(4-methylphenyl)butyl]resorcinol, 4-[1-(4-methylphenyl)hexyl]resorcinol, 4-[1-(2-methoxyphenyl)ethyl]resorcinol, 4-[1-(3-methoxyphenyl)ethyl]resorcinol, 4-[1-(4-methoxyphenyl)ethyl]resorcinol, 4-[2-(2-methoxyphenyl)ethyl]resorcinol, 4-[2-(3-methoxyphenyl)ethyl]resorcinol, 4-[2-(4-methoxyphenyl)ethyl]resorcinol, 4-[1-(4-methoxyphenyl)propyl]resorcinol, 4-[1-(4-methoxyphenyl)butyl]resorcinol, 4-[1-(4-methoxyphenyl)hexyl]resorcinol, 4-[1-(3,4-dimethylphenyl)ethyl]resorcinol, 4-[1-(3,4-dimethoxyphenyl)ethyl]resorcinol, 4-[2-(3,4-dimethylphenyl)ethyl]resorcinol, 4-[2-(3,4-dimethoxyphenyl)ethyl]resorcinol, 4-[1-(3-methoxy-4-methylphenyl)ethyl]resorcinol, 4-[2-(3-methoxy-4-methylphenyl)ethyl]resorcinol, 4-[1-(3-methyl-4-methoxyphenyl)ethyl]resorcinol, 4-[2-(3-methyl-4-methoxyphenyl)ethyl]resorcinol, 4-[1-(3-methoxy-4-methylphenyl)propyl]resorcinol, 4-[1-(3-methyl-4-methoxyphenyl)propyl]resorcinol, 4-[1-(3-methoxy-4-methylphenyl)butyl]resorcinol, 4-[1-(3-methyl-4-methoxyphenyl)butyl]resorcinol, 4-[1-(3-methoxy-4-methylphenyl)hexyl]resorcinol, 4-[1-(3-methyl-4-methoxyphenyl)hexyl]resorcinol, 4-[1-(3,5-dimethoxy-4-methylphenyl)ethyl]resorcinol, 4-[2-(3,5-dimethoxy-4-methylphenyl)ethyl]resorcinol, 4-[1-(3,5-dimethoxy-4-methylphenyl)propyl]resorcinol, 4-[1-(3,5-dimethoxy-4-methylphenyl)butyl]resorcinol, 4-[1-(3,5-dimethoxy-4-methylphenyl)hexyl]resorcinol, 4-[1-(3,4,5-trimethoxyphenyl)ethyl]resorcinol, 4-[2-(3,4,5-trimethoxyphenyl)ethyl]resorcinol, 4-[1-(3,4,5-trimethoxyphenyl)propyl]resorcinol, 4-[1-(3,4,5-trimethoxyphenyl)butyl]resorcinol, 4-[1-(3,4,5-trimethoxyphenyl)hexyl]resorcinol and their mixtures. The preferred resorcinols are 4-hexylresorcinol, 4-ethylresorcinol, 4-isopropylresorcinol, 4-butylresorcinol, and 4-(1-phenylethyl)resorcinol.

In one embodiment, the composition of the invention is a leave-on non-solid composition in the form of a personal care topical emulsion, lotion, gel, cream, or vanishing cream comprising glutathione precursor which comprises cystine, glutamate (especially pyroglutamic acid or salt thereof, e.g. sodium pyroglutamate) and one or more of 4-hexylresorcinol, 4-ethylresorcinol, 4-isopropylresorcinol, 4-butylresorcinol, and 4-(1-phenylethyl)resorcinol, at pH of 3.5 to 8.5.

In one embodiment, the composition of the invention is a leave-on non-solid composition in the form of a personal care topical emulsion, lotion, gel, cream, or vanishing cream comprising glutathione precursor which comprises cystine, glutamate (especially pyroglutamic acid or salt thereof, e.g. sodium pyroglutamate), glycine, and 4-hexylresorcinol at pH of 3.5 to 8.5, especially at pH of 5 to 8.

In one embodiment, the composition of the invention is a leave-on non-solid composition in the form of a personal care topical emulsion, lotion, gel, cream, or vanishing cream comprising glutathione precursor which comprises cystine, glutamate (especially pyroglutamic acid or salt thereof, e.g. sodium pyroglutamate), glycine, and 4-butylresorcinol at pH of 3.5 to 8.5, especially at pH of 5 to 8.

In one embodiment, the composition of the invention is a leave-on non-solid composition in the form of a personal care topical emulsion, lotion, gel, cream, or vanishing cream comprising glutathione precursor which comprises cystine, glutamate (especially pyroglutamic acid or salt thereof, e.g. sodium pyroglutamate), glycine and 4-(1-phenylethyl)resorcinol at pH of 3.5 to 8.5, especially at pH of 5 to 8.

Amounts

In one embodiment, cystine is included in an amount of from 0.001 to 2%, or in the alternative of from to 0.005 to 1%, or from 0.008 to 0.5%, or in the alternative from 0.008 to 0.4%. In one embodiment, glutamate source (preferably pyroglutamate) is included in an amount of from 0.01 to 10%, or in the alternative of from to 0.01 to 5%, or from 0.05 to 1%, or in the alternative from 0.05 to 0.5%. In one embodiment, glycine source is included in an amount of from 0.01 to 10%, or in the alternative of from to 0.01 to 5%, or from 0.01 to 1%, or in the alternative from 0.01 to 0.2%, or in the alternative from 0.01 to 0.1%. In one embodiment, resorcinol is included in an amount of from 0.001% to 3%, or in the alternative of from to 0.01 to 2%, or from 0.05 to 1.5%, or in the alternative from 0.05 to 1.2%.

The total weight of amino acids is at least twice as much as the weight of the resorcinol. In one embodiment, the weight ratio of total amino acids to resorcinol is in the range of from 3:1 to 15:1. In the alternative, the weight ratio of total amino acids to resorcinol is in the range of from 2:1 to 15:1.

Carrier

Compositions of this invention also include a cosmetically acceptable carrier. Amounts of the carrier may range from 1 to 99.9%, preferably from 70 to 95%, optimally from 80 to 90%. Among the useful carriers are water, emollients, fatty acids, fatty alcohols, thickeners and combinations thereof. The carrier may be aqueous, anhydrous or an emulsion. Preferably the compositions are aqueous, especially water and oil emulsions of the water-in-oil or oil-in-water type or multiple emulsions of the water-in-oil-in-water or oil-in-water-in-oil variety. Water when present may be in amounts ranging from 5 to 95%, preferably from about 20 to about 70%, optimally from 35 to 60% by weight.

Emollient materials may serve as cosmetically acceptable carriers. These may be in the form of silicone oils, natural or synthetic esters, hydrocarbons, alcohols and fatty acids. Amounts of the emollients may range anywhere from 0.1 to 95%, preferably between 1 and 50% by weight of the composition.

Silicone oils may be divided into the volatile and non-volatile variety. The term "volatile" as used herein refers to those materials which have a measurable vapor pressure at ambient temperature. Volatile silicone oils are preferably chosen from cyclic (cyclomethicone) or linear polydimethylsiloxanes containing from 3 to 9, preferably from 5 to 6, silicon atoms. Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from $5 \times 10^{-6}$ to $0.1$ m$^2$/s at 25° C. Among the preferred nonvolatile emollients useful in the present compositions are the polydimethyl siloxanes having viscosities from $1 \times 10^{-5}$ to about $4 \times 10^{-4}$ m$^2$/s at 25° C. Another class of nonvolatile silicones are emulsifying and non-emulsifying silicone elastomers. Representative of this category is Dimethicone/Vinyl Dimethicone Crosspolymer available as Dow Corning 9040, General Electric SFE 839, and Shin-Etsu KSG-18. Silicone waxes such as Silwax WS-L (Dimethicone Copolyol Laurate) may also be useful.

Among the ester emollients are:

a) Alkyl esters of saturated fatty acids having 10 to 24 carbon atoms. Examples thereof include behenyl neopentanoate, isononyl isonanonoate, isopropyl myristate and octyl stearate.

b) Ether-esters such as fatty acid esters of ethoxylated saturated fatty alcohols.

c) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols.

d) Wax esters such as beeswax, spermaceti wax and tribehenin wax.

e) Sugar ester of fatty acids such as sucrose polybehenate and sucrose polycottonseedate.

Natural ester emollients principally are based upon mono-, di- and tri-glycerides. Representative glycerides include sunflower seed oil, cottonseed oil, borage oil, borage seed oil, primrose oil, castor and hydrogenated castor oils, rice bran oil, soybean oil, olive oil, safflower oil, shea butter, jojoba oil and combinations thereof. Animal derived emollients are represented by lanolin oil and lanolin derivatives. Amounts of the natural esters may range from 0.1 to 20% by weight of the compositions.

Hydrocarbons which are suitable cosmetically acceptable carriers include petrolatum, mineral oil, $C_{11}$-$C_{13}$ isoparaffins, polybutenes and especially isohexadecane, available commercially as Permethyl 101A from Presperse Inc.

Fatty acids having from 10 to 30 carbon atoms may also be suitable as cosmetically acceptable carriers. Illustrative of this category are pelargonic, lauric, myristic, palmitic, stearic, isostearic, oleic, linoleic, linolenic, hydroxystearic and behenic acids and mixtures thereof.

Fatty alcohols having from 10 to 30 carbon atoms are another useful category of cosmetically acceptable carrier. Illustrative of this category are stearyl alcohol, lauryl alcohol, myristyl alcohol, oleyl alcohol and cetyl alcohol and mixtures thereof.

Thickeners or rheology modifiers can be utilized as part of the cosmetically acceptable carrier of compositions according to the present invention. Typical thickeners include crosslinked acrylates (e.g. Carbopol 982®), hydrophobically-modified acrylates (e.g. Carbopol 1382®), polyacrylamides (e.g. Sepigel 305®), acryloylmethylpropane sulfonic acid/salt polymers and copolymers (e.g. Aristoflex HMB® and AVC®), cellulosic derivatives and natural gums. Among useful cellulosic derivatives are sodium carboxymethylcellulose, hydroxypropyl methocellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Inorganics may also be utilized as thickeners, particularly clays such as bentonites and hectorites, fumed silicas, talc, calcium carbonate and silicates such as magnesium aluminum silicate (Veegum®). Amounts of the thickener may range from 0.0001 to 10%, usually from 0.001 to 1%, or from 0.01 to 0.5%.

Preferred are emollients that can be used, especially for products intended to be applied to the face, to improve sensory properties and are chosen from the group of polypropylene glycol-14 butyl ether otherwise known as Tegosoft PBE, or PPG15 stearyl ether such as Tegosoft E, other oils such as esters, specifically, isopropyl myristate, isopropyl palmitate, other oils could include castor oils and derivatives thereof.

Humectants of the polyhydric alcohol-type can be employed as cosmetically acceptable carriers. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of humectant may range anywhere from 0.5 to 50%, preferably between 1 and 15% by weight of the composition.

Skin moisturizers, e.g. hyaluronic acid and/or its precursor N-acetyl glucosamine may be included. N-acetyl glucosamine may be found in shark cartilage or shitake mushrooms and are available commercially from Maypro Industries, Inc (New York). Other preferred moisturizing agents include hydroxypropyl tri($C_1$-$C_3$ alkyl)ammonium salts. These salts may be obtained in a variety of synthetic procedures, most particularly by hydrolysis of chlorohydroxypropyl tri($C_1$-$C_3$ alkyl)ammonium salts. A most preferred species is 1,2-dihydroxypropyltrimonium chloride, wherein the $C_1$-$C_3$ alkyl is a methyl group. Amounts of the salt may range from 0.2 to 30%, and preferably from 0.5 to 20%, optimally from 1% to 12% by weight of the topical composition, including all ranges subsumed therein.

Ordinarily the $C_1$-$C_3$ alkyl constituent on the quaternized ammonium group will be methyl, ethyl, n-propyl, isopropyl or hydroxyethyl and mixtures thereof. Particularly preferred is a trimethyl ammonium group known through INCI nomenclature as a "trimonium" group. Any anion can be used in the quat salt. The anion may be organic or inorganic with proviso that the material is cosmetically acceptable. Typical inorganic anions are halides, sulfates, phosphates, nitrates and borates. Most preferred are the halides, especially chloride. Organic anionic counter ions include methosulfate, toluoyl sulfate, acetate, citrate, tartrate, lactate, gluconate, and benzenesulfonate.

Still other preferred moisturizing agents which may be used, especially in conjunction with the aforementioned ammonium salts include substituted urea like hydroxymethyl urea, hydroxyethyl urea, hydroxypropyl urea; bis(hydroxymethyl) urea; bis(hydroxyethyl) urea; bis(hydroxypropyl) urea; N,N'-dihydroxymethyl urea; N,N'-di-hydroxyethyl urea; N,N'-di-hydroxypropyl urea; N,N,N'-tri-hydroxyethyl urea; tetra(hydroxymethyl) urea; tetra (hydroxyethyl) urea; tetra(hydroxypropyl) urea; N-methyl, N'-hydroxyethyl urea; N-ethyl-N'-hydroxyethyl urea; N-hydroxypropyl-N'-hydroxyethyl urea and N,N'dimethyl-N-hydroxyethyl urea. Where the term hydroypropyl appears, the meaning is generic for either 3-hydroxy-n-propyl, 2-hydroxy-n-propyl, 3-hydroxy-i-propyl or 2-hydroxy-i-propyl radicals. Most preferred is hydroxyethyl urea. The latter is available as a 50% aqueous liquid from the National Starch & Chemical Division of ICI under the trademark Hydrovance. Amounts of substituted urea that may be used in the topical composition of this invention range from 0.01 to 20%, or from 0.5 to 15%, or from 2 to 10%.

When ammonium salt and substituted urea are used, in a most especially preferred embodiment at least from 0.01 to 25%, or from 0.2 to 20%, or from 1 to 15% humectant, like glycerine, is used. Further moisturizing agents for use herein include petrolatum and/or various aquaporin manipulating actives and/or oat kernel flour.

pH of the Composition

In one embodiment, the pH of the personal care composition is between 3.5 and 8.5. In some embodiments, the pH of the personal care composition is between pH 3.5 and pH 8. In some embodiments, the pH of the personal care composition is between pH 5 to pH 7.8. In some embodiments, the pH of the personal care composition is between 5 and 7.5.

Preferred Optional Ingredients

In some embodiments, the personal care composition, and especially a leave-on skin cosmetic composition of the present invention contains sun-screen. These are typically a combination of organic and inorganic sunscreens. It is particularly important to include both UV-A and UV-B radiation sunscreens.

UV-B sunscreen oil may be selected from the class of cinnamic acid, salicylic acid, diphenyl acrylic acid, or derivatives thereof. The UV-B sunscreen oil may include one or more of octyl salicylate, 3,3,5-trimethylcyclohexyl 2-hydroxybenzoate, ethylhexyl salicylate, 2-ethylhexyl 2-cyano-3,3-diphenyl-2-propenoate, or 2-ethylhexyl-4-methoxycinnamate (also known as octyl methoxycinnamate or "OMC"). Such UV-B sunscreen oils are typically commercially available, such as Octisalate™ (octyl salicylate), Homosalate™ (3,3,5-trimethyleyclohexyl 2-hydroxybenzoate), NeoHeliopan™ (a range of organic UV filters including OMC (Neo Heliopan AV™) and ethylhexyl salicylate (Neo Heliopan OS™)), Octocrylene™ and Milestab 3039™ (2-ethylhexyl-2-cyano-3,3-diphenyl-2-propenoate) or Parsol MCX™ (2-ethylhexyl-4-methoxycinnamate). The amount of UV-B sunscreen oil in the personal care composition may be 0.1 wt % to 20 wt %, or 0.2 wt % to 10 wt %, or 0.5 wt % to 7 wt %, or 2 wt % to 6 wt %.

The personal care composition may further include a UV-B sunscreen that is water-soluble. The water soluble UV-B sunscreen may also include phenylbezimidazole sulfonic acid (also known as ensulizole), 4-aminobenzoic acid (also known as para-aminobenzoic acid or "PABA"), or both.

The personal care composition of any one of the above embodiments may further include 0.1 wt % to 10 wt % of a UV-A sunscreen oil. The UV-A sunscreen oil may include one or more of 4-t-butyl-4'-methoxydibenzoylmethane ("avobenzone"), 2-methyldibenzoylmethane, 4-methyldibenzoyl-ethane, 4-isopropyldibenzoyl-methane, 4-tert-butyldibenzoylmethane, 2,4-dimethyldibenzoylmethane, 2,5-dimethyldibenzoylmethane, 4,4'-diisopropyldibenzoyl-methane, 2-methyl-5-isopropyl-4'-methoxy-dibenzoylmethane, 2-methyl-5-tert-butyl-4'-methoxy-dibenzoyl methane, 2,4-dimethyl-4'-methoxydibenzoylmethane, 2,6-dimethyl-4-tert-butyl-4'methoxy-dibenzoylmethane, diethylaminohydroxybenzoyl hexyl benzoate, ecamsule, or methyl anthranilate. The amount of UV-A sunscreen oil in the personal care composition may be 0.5 wt % to 7 wt %, or 1 wt % to 5 wt %.

Additional suitable sunscreen oils suitable for use in the personal care composition include those commercially available from BASF corporation: Uvinul T-150 (Ethylhexyl triazone; a UV-B sunscreen oil), Uvinul A Plus (Diethylamino hydroxybenzoyl hexyl benzoate; a UV-A sunscreen oil), Tinosorb S (bis-ethylhexyloxyphenol methoxyphenyl triazine; a UV-A and UV-B sunscreen oil), Tinosorb M(methylene bisbenzotriazolyl tetramethylbutylphenol; a UV-A and UV-B sunscreen oil). Bisdisulizone disodium may also be included in the personal care composition.

A particularly preferred combination of UV-A and UV-B sunscreen oils is avobenzone and 2-ethylhexyl-4-methoxycinnamate.

In some embodiments, the sunscreen is an inorganic sunscreen. Examples of inorganic sunscreens suitable for use in the skin care composition of the present invention include, but are not limited to, microfine titanium dioxide, zinc oxide, polyethylene and various other polymers. By the term "microfine" is meant particles of average size ranging from 10 to 200 nm, alternatively from 20 to 100 nm. Amounts of the sunscreen when present in a skin care formulation according to some embodiments of the present invention may range from 0.1% to 30%, alternatively from 2% to 20%, alternatively from 4% to 10%.

It has been taught that selenium source, e.g. selenomethionine, is an essential ingredient, along with constituent amino acids of GSH, for enabling GSH intracellular biosynthesis; the transsulfuration pathway (also called the cystathionine pathway) allows the utilization of methionine for GSH synthesis Surprisingly, it has been found as part of the present invention, however, that a selenium source is not necessary, and is indeed superfluous, to achieve intracellular increase in GSH content according to the present invention. Although selenium source may be included, it is preferably avoided in topical skin care compositions of the invention because it is considered a skin sensitizer under some regulatory regimes. Accordingly, the amount of selenium in the present compositions is from 0 to maximum 0.1%, or at most 0.05%, optimally no more than 0.01%.

The inventive composition preferably includes a skin lightening compound, in addition to resorcinols included herein, to obtain optimum skin lightening performance at an optimum cost. Illustrative substances are additional resorcinols (2,5-disubstituted, 4,5-disubstituted, and 4,6 di-substituted), placental extract, lactic acid, niacinamide, arbutin, kojic acid, ferulic acid, hydroquinone, resorcinol derivatives including di-substituted resorcinols and combinations thereof. More preferably, such skin lightening compound is a tyrosinase inhibitor, most preferably a compound selected from the group consisting of kojic acid, hydroquinone and other (non-4 substituted resorcinols). Also, dicarboxylic acids represented by the formula HOOC—$(C_xH_y)$—COOH where x=4 to 20 and y=6 to 40 such as azelaic acid, sebacic acid, oxalic acid, succinic acid, fumaric acid, octadecenedioic acid (e.g. Arlatone DC) or their salts or a mixture thereof, most preferably fumaric acid or salt thereof, especially di-sodium salt. It has been found that combination with 12 HSA with fumaric acid or salts thereof are particularly preferred, especially for skin lightening formulations. Amounts of these agents may range from 0.1 to 10%, preferably from 0.5 to 2%. It is preferred that the skin lightening coactive according to the invention is vitamin 83 or a derivative thereof and is selected from the group consisting of niacinamide, nicotinic acid esters, non-vasodilating esters of nicotinic acid, nicotinyl amino acids, nicotinyl alcohol esters of carboxylic acids, nicotinic acid N-oxide, niacinamide N-oxide and mixtures thereof.

Another preferred ingredient of the inventive compositions is a retinoid. As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably retinol, retinol esters (e.g., $C_2$-$C_{22}$ alkyl esters of retinol, including retinyl palmitate, retinyl acetate, retinyl propionate), retinal, and/or retinoic acid (including all-trans retinoic acid and/or 13-cis-retinoic acid), more preferably retinoids other than retinoic acid. These compounds are well known in the art and are commercially available from a number of sources, e.g., Sigma Chemical Company (St. Louis, Mo.), and Boerhinger Mannheim (Indianapolis, Ind.). Other retinoids which are useful herein are described in U.S. Pat. No. 4,677,120, issued Jun. 30, 1987 to Parish et al.; U.S. Pat. No. 4,885,311, issued Dec. 5, 1989 to Parish et al.; U.S. Pat. No. 5,049,584, issued Sep. 17, 1991 to Purcell et al.; U.S. Pat. No. 5,124,356, issued Jun. 23, 1992 to Purcell et al.; and U.S. Pat. No. Reissue 34,075, issued Sep. 22, 1992 to Purcell et al. Other suitable retinoids are tocopherylretinoate [tocopherol ester of retinoic acid (trans- or cis-), adapalene {6-[3-(1-adamantyl)-4-methoxyphenyl]-2-naphthoic acid}, and tazarotene (ethyl 6-[2-(4,4-dimethylthiochroman-6-yl)-ethynyl]nicotinate). Preferred retinoids are retinol, retinyl palmitate, retinyl acetate, retinyl propionate, retinal and combinations thereof. The retinoid is preferably substantially pure, more preferably essentially pure. The compositions of this invention may contain a safe and effective amount of the retinoid, such that the resultant composition is safe and effective for regulating keratinous tissue condition, preferably for regulating visible and/or tactile discontinuities in skin, more preferably for regulating signs of skin aging, even more preferably for regulating visible and/or tactile discontinuities in skin texture associated with skin aging. The compositions preferably contain from 0.005% to 2%, or from 0.01% to 2%, retinoid. Retinol is preferably used in an amount of 0.01% to 0.15%; retinol esters are preferably used in an amount of from 0.01% to 2% (e.g., 1%); retinoic acids are preferably used in an amount of 0.01% to 0.25%; tocopheryl-retinoate, adapalene, and tazarotene are preferably used in an amount of from 0.01% to 2%.

A variety of herbal extracts may optionally be included in compositions of this invention. Illustrative are pomegranate, white birch (*Betula alba*), green tea, chamomile, licorice and extract combinations thereof. The extracts may either be water soluble or water-insoluble carried in a solvent which respectively is hydrophilic or hydrophobic. Water and ethanol are the preferred extract solvents.

Also included may be such materials as resveratrol, alpha-lipoic acid, ellagic acid, kinetin, retinoxytrimethylsilane (available from Clariant Corp. under the Silcare 1M-75 trademark), dehydroepiandrosterone (DHEA) and combinations thereof. Ceramides (including Ceramide 1, Ceramide 3, Ceramide 3B, Ceramide 6 and Ceramide 7) as well as pseudoceramides may also be utilized for many compositions of the present invention but may also be excluded. Amounts of these materials may range from 0.000001 to 10%, preferably from 0.0001 to 1%.

The personal care composition may further include about 0.1 wt % to about 8 wt % of a film forming polymer. Such film-forming polymers include, but are not limited to, polyalkyleneoxy terminated polyamides (e.g., INCI name: Polyamide-3, Polyamide-4), polyether polyamides (e.g., INCI name: Polyamide-6), mixed acid terminated polyamides (e.g., INCI name: Polyamide-7), and ester terminated poly (ester-amides) (e.g., INCI name: Polyamide-8). Such film forming polymers may be synthesized or are available commercially, such as under the Sylvaclear™ line of products by Arizona Chemical Company, LLC and the OleoCraft™ line of products by Croda International PLC. Film-forming polymers also include, but are not limited to, the INCI named Polyester-5 (e.g., Eastman AQ™ 38S Polymer), PPG-17/IPDI/DMPA Copolymer (e.g., Avalure™ UR 450 Polymer), Acrylates Copolymer (e.g., Avalure™ AC 120 Polymer), and polysaccharides such as Xilogel (tamarin gum), lotus bean gums, tara gum, beta glucan, pullulan, carboxymethyl cellulose, hydroxypropyl cellulose, sodium alginate, potato starch, carrageenan. The film forming polymer may include combinations of any two or more of the polymers recited above. The amount of film forming polymer in the personal care composition may be 0.1 wt % to 8 wt %.

Preservatives can desirably be incorporated into the compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are iodopropynyl butyl carbamate, phenoxyethanol, caprylyl glycol, $C_{1-6}$ parabens (especially, methyl paraben and/or propyl paraben), imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2%. An especially preferred combination is octocrylene and caprylyl glycol, since caprylyl glycol has been disclosed to enhance UVA and UVB protection.

Anti-fungal agents suitable for inclusion in personal care compositions are well known to one of skill in the art. Examples include, but are not limited to, climbazole, ketoconazole, fluconazole, clotrimazole, miconazole, econazole, etaconazole, terbinafine, salts of any one or more of these (e.g., hydrochloride salts), zinc pyrithione, selenium disulfide, and combinations of any two or more thereof.

In some embodiments, the personal care compositions of the present invention include vitamins. Illustrative vitamins are Vitamin A (retinol), Vitamin B2, Vitamin B3 (niacin), Vitamin B6, Vitamin B12, Vitamin C, Vitamin D, Vitamin E, Vitamin K and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. In some embodiments, the Vitamin B6 derivative is Pyridoxine Palmitate. In some embodiments, the Vitamin B3 derivative is nicotinamide riboside. Flavonoids may also be useful, particularly glucosyl hesperidin, rutin, and soy isoflavones (including genistein, daidzein, equol, and their glucosyl derivatives) and mixtures thereof. Total amount of vitamins or flavonoids when present may range from 0.0001% to 10%, alternatively from 0.001% to 10%, alternatively from 0.01% to 10%, alternatively from 0.1% to 10%, alternatively from 1% to 10%, alternatively from 0.01% to 1%, alternatively from 0.1% to 0.5%.

In some embodiments, the personal care compositions of the present invention include an enzyme such as, for example oxidases, proteases, lipases and combinations thereof. In some embodiments, the personal care compositions of the present invention includes superoxide dismutase, commercially available as Biocell SOD from the Brooks Company, USA.

In some embodiments, the personal care compositions of the present invention include desquamation promoters. In some embodiments, the personal care compositions of the present invention include desquamation promoters at a concentration from 0.01% to 15%, alternatively from 0.05% to 15% alternatively from 0.1% to 15%, alternatively from 0.5% to 15%

Illustrative desquamation promoters include monocarboxylic acids. Monocarboxylic acids may be substituted or unsubstituted with a carbon chain length of up to 16. In some embodiments, the carboxylic acids are the alpha-hydroxycarboxylic acids, beta-hydroxycarboxylic or polyhydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids include glycolic, lactic malic and tartaric acids. In some embodiments, the salt is ammonium lactate. In some embodiments, the beta-hydroxycarboxylic acid is salicylic acid. In some embodiments, the phenolic acids include ferulic acid, salicylic acid, kojic acid and their salts.

In some embodiments, the at least one additional component may be present from 0.000001% to 10%, alternatively from 0.00001% to 10%, alternatively from 0.0001% to 10%, alternatively from 0.001% to 10%, alternatively from 0.01% to 10%, alternatively from 0.1% to 10%, alternatively from 0.0001% to 1% by weight of the composition. Colorants, opacifiers or abrasives may also be included in compositions of the present invention. The colorants, opacifiers or abrasives may be included at a concentration from 0.05% to 5%, alternatively between 0.1% and 3% by weight of the composition.

In some embodiments, the personal care product of the present invention may also include a peptide, such as, for example, the commercially available pentapeptide derivative—Matrixyl™, which is commercially available from Sederma, France. In another example, in some embodiments, the personal care product of the present invention may also include Carnosine.

The compositions of the present invention can comprise a wide range of other optional components. The CTFA Cosmetic Ingredient Handbook, Second Edition, 1992, which is incorporated by reference herein in its entirety, describes a wide variety of non-limiting cosmetic and pharmaceutical ingredients commonly used in the topical cosmetic skin care industry, which are suitable for use in the compositions of the present invention. Examples include: antioxidants, binders, biological additives, buffering agents, colorants, thickeners, polymers, astringents, fragrance, humectants, opacifying agents, conditioners, exfoliating agents, pH adjusters, preservatives, natural extracts, essential oils, skin sensates, skin soothing agents, and skin healing agents.

Form of the Composition

The compositions of the present invention are preferably non-solid. The compositions of the invention are preferably leave-on compositions. The compositions of the present invention are preferably leave-on compositions to be applied to remain on the skin. These leave-on compositions are to be distinguished from compositions which are applied to the skin and subsequently removed either by washing, rinsing, wiping, or the like either after or during the application of the product. Surfactants typically used for rinse-off compositions have physico-chemical properties giving them the ability to generate foam/lather in-use with ease of rinse; they can consist of mixtures of anionic, cationic, amphoteric, and nonionic. Surfactants used in leave-on compositions on the other hand are not required to have such properties. Rather, as leave-on compositions are not intended to be rinsed-off they need to be non-irritating and therefore it is necessary to minimize the total level of surfactant and the total level of anionic surfactant in leave-on compositions. The total level of surfactant in the inventive compositions is preferably from 1% no more than 15%, more preferably below 10%, most preferably at most 9%, optimally at most 6%.

In some embodiments, anionic surfactants are present in the leave-on skin care composition in an amount of 0.01% to at most 5% by weight of the composition, alternatively from 0.01% to 4% by weight of the composition, alternatively from 0.01% to 3% by weight of the composition, alternatively from 0.01% to 2% by weight of the composition, alternatively substantially absent (less than 1%, or less than 0.1%, or less than 0.01%). In some embodiments, the total level of surfactant in the skin care compositions is no more than 15%, alternatively below 10%, alternatively at most 9%.

In some embodiments, the surfactant is selected from the group consisting of anionic, nonionic, cationic and amphoteric actives.

In some embodiments, nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. In some embodiments, the non-ionic surfactant is selected from the group consisting of alkyl polyglycosides, saccharide fatty amides (e.g. methyl gluconamides) and trialkylamine oxides.

Amphoteric surfactants suitable in skin care compositions according to some embodiments of the present invention include cocoamidopropyl betaine, $C_{12}$-$C_{20}$ trialkyl betaines, sodium lauroamphoacetate, and sodium laurodiamphoacetate.

Anionic surfactants suitable in skin care compositions according to some embodiments of the present invention include soap, alkyl ether sulfates and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, $C_8$-$C_{20}$ sarcosinates, $C_8$-$C_{20}$ acyl lactylates, sulfoacetates and combinations thereof.

The compositions of the present invention are typically in the form of emulsions, which may be oil-in-water, or water-in-oil. In some embodiments the personal care compositions are vanishing creams and creams or lotions based on an oil-in-water emulsion. Vanishing cream base is one which comprises 5 to 40% fatty acid and 0.1 to 20% soap. In such creams, the fatty acid is preferably substantially a mixture of stearic acid and palmitic acid and the soap is preferably the potassium salt of the fatty acid mixture, although other counterions and mixtures thereof can be used. The fatty acid in vanishing cream base is often prepared using hysteric acid which is substantially (generally about 90 to 95%) a mixture of stearic acid and palmitic acid. A typical hysteric acid comprises about 52-55% palmitic acid and 45-48% stearic acid of the total palmitic-stearic mixture. Thus, inclusion of hysteric acid and its soap to prepare the vanishing cream base is within the scope of the present invention. It is particularly preferred that the composition comprises higher than 7%, preferably higher than 10%, more preferably higher than 12% fatty acid. A typical vanishing cream base is structured by a crystalline network and is sensitive to the addition of various ingredients.

In one embodiment, the personal care composition is formulated as a water-in-oil emulsion with cystine substantially solubilized in the aqueous phase. In one embodiment, the personal care composition is formulated as a water-in-oil emulsion with cystine in the aqueous droplets, with at least 90% of the droplets having a diameter in the range of from 100 nm to 20 microns, or in the alternative from 200 nm to 20 microns, or to 10 microns.

In some embodiments, in addition to containing the GSH precursor, the personal care composition is formulated as a facial mask. In some embodiments, in addition to containing the GSH precursor, the personal care composition is formulated as a facial mask according to the formulations described in U.S. Pat. No. 5,139,771. In some embodiments, in addition to containing the GSH precursor, the personal care composition is formulated as a facial mask according to U.S. Pat. No. 4,933,177. In some embodiments, in addition to containing the GSH precursor, the personal care composition is formulated as a facial mask according to the formulations described in U.S. Pat. No. 6,001,367.

In some embodiments, in addition to containing the GSH precursor, the personal care composition is formulated as a shampoo. In some embodiments, the personal care compositions of the present invention are formulated as a deodorant. In some embodiments, in addition to containing the GSH precursor, the personal care composition is formulated as a deodorant according to the formulations described in U.S. Pat. No. 7,282,471. In some embodiments, the personal care compositions of the present invention are formulated as an antiperspirant. In some embodiments, in addition to containing the GSH precursor, the personal care composition is formulated as an antiperspirant according to the formulations described in U.S. Pat. No. 7,282,471.

In some embodiments, the personal care compositions of the present invention are formulated as a single use personal care towelette product. In some embodiments, in addition to containing the GSH precursor, the personal care composition is formulated as a single use personal care towelette product according to the formulations described in U.S. Pat. No. 7,282,471.

In some embodiments, the personal care compositions of the present invention are formulated as a soap bar. In some embodiments, in addition to containing the GSH precursor, the personal care composition is formulated as a soap bar according to the formulations described in U.S. Pat. No. 7,282,471.

Methods of Making Skin Care Compositions

In some embodiments, skin care compositions according to the present invention can be made by:
a. mixing all water soluble ingredients including preservatives, thickening polymer, optionally glycerine, and water;
b. heating the mixture to a temperature of 70-90° C.;
c. mixing all the oil soluble ingredients and the compound of formula (1) to a temperature of 70-90° C.;
d. adding the mixed oil soluble ingredients to the heated mixture of water soluble ingredients, and mixing via agitation, maintaining the mixture at a temperature of 70-90° C.; and
e. cooling the mixture to room temperature, whilst mixing.

In some embodiments the personal care compositions of the invention are prepared by making an emulsion:
a. solubilizing cystine at the desired level in high pH (9 to 14, or 9 to 12) aqueous solution
b. preparing a macroemulsion in oil with this solution with an emulsifier, then
c. adding, with mixing, an acidic aqueous solution to obtain an emulsion with pH within a neutral range required for the topical composition and, lastly,
d. subjecting the emulsion to high shear, or homogenization, or sonolation step e.g. via a homogenizer_such as Nano DeBee homogenizer of BEE International (Massachusetts, USA) or a Sonolator homogenizer manufactured by Sonic Corporation (Connecticut, USA), to produce a homogeneous neutral pH range final emulsion with more than 90% of the droplets having a diameter in the size range of from 100 nm to 20 microns.

Method of Using the Skin Care Compositions

In some embodiments, the skin care composition is topically applied to human skin. In some embodiments, the skin care composition provides at least one benefit, selected from the group consisting of: skin conditioning, skin smoothening, reduction of wrinkled or aged skin, reduction of inflammation of the skin, reduction of dryness, reduction of age spots, reduction of sun burn, and lightening of the skin.

In some embodiments, a small quantity of the skin care composition, for example from 1 to 5 ml, is applied to exposed area of the skin, from a suitable container or applicator and, if necessary, it is then spread over and/or rubbed into the skin using the hand or fingers or a suitable device.

Reference is now made to the following examples, which together with the above descriptions illustrate some embodiments of the invention in non-limiting examples.

EXAMPLES

Experimental Methods

Powders of the following amino acids (pyroglutamic acid and glycine) were purchased from Sigma, and individual stock solutions of each amino acid prepared by reconstitution of the powder in water (pH 7). All amino acids were L stereo isomers. Cystine (Sigma) stock solutions were generated in 0.5M sodium hydroxide (pH 12) as cystine is poorly soluble in neutral solutions. Cystine esters, ditert-butyl L-cystinate dihydrochloride (DTBC) and diethyl L-cystinate dihydrochloride (DEC) were purchased from Bachem; L-Cystine dimethyl ester dihydrochloride (CDME) was from Sigma. Sodium pyroglutamic acid (also known as sodium pyrrolidone carboxylate (NaPCA)) was supplied as a 50% solution in water from Ajinomoto. To generate the mixture henceforth described as GAP, appropriate volumes of three amino acids (glutamate source (i.e NaPCA), cystine, and glycine) were combined in Hank's Balanced Salt Solution (Sigma) such that the glutamate source, cystine, and glycine were in a 0.5:1:1 weight ratio. The specific concentrations used in each assay are referenced below.

Additional test reagents: 4-ethylresorcinol (Alfa Aesar, Sigma-Aldrich, and TCI), 4-hexylresorcinol (Sigma-Aldrich), 4-butylresorcinol (ViviMed Labs and TCI), 4-isopropylresorcinol (AV Square Chem), 4-(1-phenylethyl)resorcinol (Symrise Inc. and TCI), 4-methylresorcinol (Sigma-Aldrich), olivetol (Sigma-Aldrich), 3-hydroxytyrosol (Sigma-Aldrich and TCI), and 4-(cyclohexylmethyl)resorcinol (prepared as described in U.S. Pat. No. 7,468,464). These reagents were typically solubilized in ethanol or dimethyl sulfoxide. In assays below, appropriate volumes were added to vehicle control samples to normalize for potential solvent effects.

Glutathione Assay

Aged Human Keratinocytes (Cascade Biologics, now ThermoFisher Scientific, Waltham, Mass.) were maintained in EpiLife® medium containing 60 uM calcium chloride and 1% Human Keratinocyte Growth Supplement (both media components from ThermoFisher Scientific) in a humidified incubator with an atmosphere containing 5% $CO_2$ at 37° C. The medium was refreshed every 2-3 days. Subsequently, cells were trypsinized at 90% confluency and seeded at a density of $1 \times 10^4$ per well into 96-well plates with white wall and clear bottom. One or two days after seeding, cell medium was replaced with Hank's Balanced Salt Solution (HBSS), and keratinocytes were pre-treated with GAP (or 0.12-0.240 mM sodium hydroxide vehicle control, pH 7.5) alone or in combination with additional test reagents described above or L-cystine esters alone for 1-2 hours. The concentration of all amino acids constituting the GAP mixture used in this assay are designated in the data tables, and fully described in the abbreviations list below.

After one or two hours of pre-treatment with GAP or additional test reagents, alone or in combination, keratinocytes were then challenged with 25 uM menadione (Sigma-Aldrich), a known inducer of oxidative stress. After 18-20 hours, cells were harvested and analyzed for total glutathione levels using a commercially available kit (GSH-GSSG GLo Assay, Promega), a luminescence-based system for the detection and quantification of total glutathione in cultured cells. In summary, after cell treatment, the media was removed and replaced with a cell lysis reagent for 5 minutes at 20-25° C.; note, all remaining steps were also conducted at 20-25° C. Next, a luciferase generation reagent was added to each well and incubated for 30 minutes. Following this step, a luciferin detection reagent was added to each well and plates were incubated for 15 minutes. Finally, plates were then read for luminescence in a FlexStation 3 plate reader (Molecular Devices). Total glutathione levels were calculated after interpolation of glutathione concentrations from a standard curve. Experimental conditions were typically conducted in at least triplicate determinations. Statistical significance was calculated using 1-way ANOVA. Percent protection was calculated by using the calculated glutathione levels from each experiment in the following equation:

$$\frac{(\text{Test sample}) - (\text{vehicle control} + \text{menadione})}{\text{vehicle control}} \times 100\% = \% \text{ protection}$$

Reactive Oxygen Species (RSO) Assay

Human Keratinocytes (Promocell, Heidelberg, Germany) were maintained in EpiLife® keratinocyte medium containing 60 uM calcium chloride and 1% Human Keratinocyte Growth Supplement (HKGS) in a humidified incubator with an atmosphere containing 5% CO2 at 37° C. The medium was refreshed every other day. Subsequently, cells were trypsinized at 90% confluency and seeded at a density of $1\text{-}2 \times 10^4$ per well into 96-well plates with black wall and clear bottom. On the second day after seeding, cell medium was replaced with Hank's Balanced Salt Solution (HBSS) with or without menadione (10-25 uM), GAP (typically at 49 uM pyroglutamic acid, 60 uM cystine, 194 uM glycine), GAP vehicle (0.2 mM NaOH, pH 7.5), above-described additional test reagents, or combinations of GAP with additional test reagents or L-cystine esters alone, and incubated for additional 18 hours. For ROS detection, CellROX green (Life Tech, Thermo Fisher Scientific, Rockford, USA) reagent was added into each well to a final concentration of 15-25 uM and incubated for additional 2-4 hours at 37° C. in a humidified incubator. The ROS fluorescence was detected using a Tecan microplate reader (Excitation/Emission=490/525). Relative ROS production was calculated with normalization based on the vehicle control treatment which was set to 100%. Where indicated, percent protection was calculated as a comparison to menadione alone treatment, using the measured relative fluorescent units in the following equation:

$$\frac{(\text{Vehicle control} + \text{Menadione}) - (\text{Test Sample})}{(\text{vehicle control} + \text{menadione})} \times 100\% = \% \text{ protection}$$

ROS levels were evaluated together with cell viability because it is possible to get a false negative for ROS if treatment is so toxic, that at the time of assay, cells are dead (and there are no longer any detectable ROS). Decrease in ROS levels is meaningful if cells are still viable.

Cell Viability Assay

Human Keratinocytes (Promocell, Heidelberg, Germany) were maintained in EpiLife® keratinocyte medium containing 60 uM calcium chloride and 1% Human Keratinocyte Growth Supplement (HKGS). The medium was refreshed every other day. Subsequently, cells were trypsinized at 90% confluency and seeded at a density of $2 \times 10^4$ per well into 96-well transparent tissue culture plates. On the second day after seeding, cell medium was replaced with treatments as described above in ROS assay section. After 18 hours, Cell Culture Kit-8 (CCK-8) reagent (Dojindo, Kumamoto, Japan) was diluted 1:10 in HBSS and incubated with cells for 4 h at 37° C. in a humidified incubator. Optical absorption at 450 nm was measured using a Tecan Safire2 plate reader. Relative viability was calculated with normalization based on the vehicle control treatment, which was set to 100%.

Where indicated, percent protection was calculated as a comparison to menadione alone treatment, using the measured relative absorbance units in the following equation:

$$\frac{\text{Test Sample} - (\text{vehicle control} + \text{menadione})}{(\text{vehicle control} + \text{menadione})} \times 100\% = \% \text{ protection}$$

Tyrosinase Activity Assay

Human primary melanocytes (Cascade Biologics, now ThermoFisher Scientific) were grown in melanocytes growth medium (MGM) with human melanocyte growth supplement (both media components from ThermoFisher Scientific). Melanocytes were seeded at $1 \times 10^4$ cells/well in a 96 wells plate and cultures left undisturbed for 24 hrs in a 5% $CO_2$ humidified incubator at 37° C. At 24 hrs post-seeding, cells were treated with GAP amino acids (consisting of glutamine (32 LIM), cystine (40 uM), glycine (129 uM)) alone or in combination with test reagents described above, and left undisturbed for another 72 hours, Subsequently, cell viability was assessed and the cells were then lysed and progressed for determination of in situ tyrosinase activity. Cultures were rinsed twice with 1× phosphate-buffered saline and lysed with 40 uL of 0.5% TritonX 100 for 1 hour on an ice bed. In situ tyrosinase activity was visualized by addition of 60 μl of 50 mM potassium phosphate buffer (pH 6.8) containing 2 mM DOPA (3,4dihydroxy phenylalanine) and 4 mM MBTH reagent (3-Methyl-2-Benzothiazolinone hydrazone hydrochloride) for 1 hour at 37° C. The reaction was stopped by the addition of 100 uL of ice-cold 10% tricholoracetic acid and then centrifuged at approximately 300 g for 10 minutes at 4° C. The soluble supernatant was separated from the pellet and the optical density read in a TECAN plate-reader (540 nm filter). The spectrophotometric optical density at 540 nm for untreated cells (no active) is considered as 100% tyrosinase activity. Tyrosinase activity is expressed after correction for cell numbers (activity/viability) and represented as % control.

Abbreviations in the Examples are as follows:
mM=millimolar
uM=micromolar
uL=micro liter
GAP=glutamate and cystine and glycine mix
GAP 5=4 uM sodium pyroglutamic acid, 5 uM cystine, 16 uM glycine
GAP 10=8 uM sodium pyroglutamic acid, 10 uM cystine, 32 uM glycine
GAP 20=16 uM sodium pyroglutamic acid, 20 uM cystine, 64 uM glycine
NaPCA=sodium pyroglutamic acid (also known as sodium pyrrolidonecarboxylic acid)
HR=4-hexylresorcinol
BR=4-butylresorcinol
IPR=4-isopropylresorcinol
ER=4-ethylresorcinol
PER=4-(1-phenylethyl)resorcinol
MR=4-methylresorcinol
4-CHMR=4-(cyclohexylmethyl)resorcinol
DEC=Diethyl L-cystinate dihydrochloride
CDME=L-Cystine dimethyl ester dihydrochloride
DTBC=Ditert-butyl L-cystinate dihydrochloride Example 1

Example 1 evaluated various combinations of 4-alkyl resorcinols and amino acids constituting GSH building blocks for potentiating intracellular GSH production. Results that were obtained are summarized in Tables 1A and 1B.

In Tables 10 through 1H the efficacy of various cystine esters was also tested.

TABLE 1A

Glutathione Synthesis

| Sample | | Mean (uM glutathione) | % Protection (improvement vs. vehicle control + menadione) |
|---|---|---|---|
| A | Vehicle Control | 1.75 | |
| B | Vehicle Control + menadione | 0.07[1] | 0[1] |
| Test Samples | | | |
| C | GAP 10 + menadione | 1.34[1, 2, 3] | 72[1, 2, 3] |
| D | GAP 20 + menadione | 4.61[2, 3] | 259[2, 3] |
| E | HR (20 uM) + menadione | 0.46[1] | 22[1] |
| F | HR (20 uM) + cystine + menadione | 2.81[1, 2, 3] | 156[1, 2, 3] |
| 1 | HR (20 uM) + GAP 10 (NaPCA + glycine + cystine) + menadione | 4.00[2, 3] | 224[2, 3] |
| 2 | HR (20 uM) + NaPCA + cystine + menadione | 4.20[2, 3] | 236[2, 3] |
| 3 | HR (20 uM) + glycine + cystine + menadione | 3.64[2, 3] | 204[2, 3] |

Staistically significant decrease:
[1]p < 0.05 compared to HR + GAP10 + menadione
Statistically significant improvement:
[2]p < 0.05 compared to vehicle control + menadione
[3]p < 0.05 compared to HR + menadione Samples A through G were outside the scope of the invention. Sample D was a positive control as it employed a high concentration of GAP. It can be seen from the results in Table 1A that a combination of HR with cystine and glutamate (Samples 1 and 2 within the scope of the invention) or with cystine and glycine (Sample 3) resulted in synergistic increase in GSH synthesis compared to the GSH synthesis achieved with either resorcinol or GAP alone (Samples E and C, respectively), or combination of HR with cystine alone (Sample G). Samples 1 to 3 performed on par with positive control (Sample D), yet at lower concentration of GAP and therefore at lower concentration of cystine, therefore counterbalancing the problem of having to solubilize relatively high amounts of cystine.

TABLE 1B

Glutathione Synthesis

| Sample | | Mean (uM glutathione) | % Portection (improvement vs. vehicle control + menadione) |
|---|---|---|---|
| A | Vehicle Control | 1.75 | |
| B | Vehicle Control + menadione | 0.07[1] | 0 |
| Test Samples | | | |
| C | GAP 10 + menadione | 1.34[1, 2, 3] | 72[1, 2, 3] |
| D | GAP 20 + menatione | 4.61[2, 3] | 259[2, 3] |
| E | BR (50 uM) + menadione | 0.06[1] | −1[1] |
| F | BR (50 uM) + glycine + cystine + menadione | 1.25[1, 2, 3] | 67[2, 3] |
| G | BR (50 uM) + cystine + menadione | 1.73[2, 3] | 95[2, 3] |
| 1 | BR (50 uM) + GAP 10 (NaPCA + glycine + cystine) + menadione | 2.22[2, 3] | 122[2, 3] |
| 2 | BR (50 uM) + NaPCA + cystine + menadione | 2.27[2,3] | 125[2,3] |

Staistically significant decrease:
[1]p < 0.05 compared to BR + GAP10 + menadione
Statistically significant improvement:
[2]p < 0.05 compared to vehicle control + menadione
[3]p < 0.05 compared to BR + menadione Samples marked by alphabetical characters (A through H above) were outside the scope of the invention. Numerically marked samples were within the scope of the invention. Sample D was a positive control as it employed a high concentration of GAP. It can be seen from the results in Table 1B that when 4-alkyl resorcinol is BR, unlike in Table 1A with HR, both cystine and glutamate appear to be needed (but not glycine) to achieve synergistic increase in GSH synthesis: Samples 1 and 2, within the scope of the invention, resulted in synergistic increase in GSH synthesis compared to the GSH synthesis achieved with either BR or GAP alone (Samples E and C, respectively), or combination of the BR with cystine alone (Sample G) or combination of BR with cystine and glycine, without glutamate (Sample F).

Samples 1 and 2 within the scope of the invention achieved about double GSH synthesis improvement compared with Samples E, C, F, and G.

TABLE 1C

Glutathione Synthesis

| Sample | | Mean (μm glutathione) | % Protection (improvement vs. vehicle control + menadione) |
|---|---|---|---|
| A | Vehicle control | 2.73 | |
| B | Vehicle control + Menadione | 0.18[1] | 0 |
| C | DEC (40 uM) + Menadione | 0.54[1,2] | 13[1,2] |
| D | DEC (80 uM) + Menadione | 2.72[2] | 93[2] |

Statistically significant decrease:
[1] $p < 0.05$ compared to vehicle control
Statistically significant improvement:
[2] $p < 0.05$ compared to vehicle control + menadione

TABLE 1D

Reduction in Reactive Oxygen Species

| Sample | ROS inhibition (% of vehicle control) | % Protection (improvement vs. vehicle control + menadione) | Cell viability (% of vehicle control) | % protection (improvement vs. vehicle control + menadione) |
|---|---|---|---|---|
| Vehicle control | 100 | | 100 | |
| Vehicle control + Menadione | 375.5[1] | | 73.7[1] | |
| DEC (20 uM) + Menadione | 232.8[1,2] | 38.0[1,2] | 109.8[2] | 48.9[2] |
| DEC (40 uM) + Menadione | 211.9[1,2] | 43.6[1,2] | 127.3[1,2] | 72.7[1,2] |
| DEC (80 uM) + Menadione | 233.8[1,2] | 37.7[1,2] | 131.5[1,2] | 78.3[1,2] |
| DEC (160 uM) + Menadione | 253.8[1,2] | 32.4[1,2] | 122.3[1,2] | 65.9[1,2] |

Statistically significant difference:
[1] $p < 0.05$ compared to vehicle control
Statistically significant difference:
[2] $p < 0.05$ compared to vehicle control + menadione

TABLE 1E

Glutathione Synthesis

| | Sample | Mean (μm glutathione) | % Protection (improvement vs. vehicle control + menadione) |
|---|---|---|---|
| A | Vehicle control | 2.73 | |
| B | Vehicle control + Menadione | 0.18[1] | 0 |
| C | DTBC (40 uM) + Menadione | 0.17[1] | 0[1] |
| D | DTBC (80 uM) + Menadione | 0.19[1] | 1[1] |

Statistically significant decrease:
[1] $p < 0.05$ compared to vehicle control

TABLE 1F

Reduction in Oxygen Species

| Sample | ROS inhibition (% of vehicle control) | % Protection (improvement vs. vehicle control + menadione) | Cell viability (% of vehicle control) | % protection (improvement vs. vehicle control + menadione) |
|---|---|---|---|---|
| Vehicle control | 100 | | 100 | |
| Vehicle control + Menadione | 375.5[1] | | 73.7[1] | |
| DTBC (20 uM) + Menadione | 367.0[1] | 2.2 | 78.1[1] | 6.0[1] |
| DTBC (40 uM) + Menadione | 323.7[1,2] | 13.8[1,2] | 75.91 | 3.0[1] |
| DTBC (80 uM) + Menadione | 268.7[1,2] | 28.4[1,2] | 73.61 | −0.1[1] |
| DTBC (160 uM) + Menadione | 221.1[1,2] | 41.1[1,2] | 104.2[2] | 41.3[2] |

Statistically significant difference:
[1] $p < 0.05$ compared to vehicle control
Statistically significant difference:
[2] $p < 0.05$ compared to vehicle control + menadione

TABLE 1G

Glutathione Synthesis

| | Sample | Mean (μm glutathione) | % Protection (improvement vs. vehicle control + menadione) |
|---|---|---|---|
| A | Vehicle control | 2.96 | |
| B | Vehicle control + Menadione | 0.18[1] | 0 |
| C | CDME (80 uM) + Menadione | 1.09[1,2] | 31[1,2] |

Statistically significant decrease:
[1] $p < 0.05$ compared to vehicle control
Statistically significant improvement:
[2] $p < 0.05$ compared to vehicle control + menadione

TABLE 1H

Reduction in Oxygen Species

| Sample | ROS inhibition (% of vehicle control) | % Protection (improvement vs. vehicle control + menadione) | Cell viability (% of vehicle control) | % protection (improvement vs. vehicle control + menadione) |
|---|---|---|---|---|
| Vehicle control | 100 | | 100 | |
| Vehicle control + Menadione | 131.8[1] | | 69.8[1] | |
| CDME (20 uM) + Menadione | 107.8[2] | 18.2[2] | 90.9[1,2] | 30.2[1,2] |
| CDME (40 uM) + Menadione | 111.3[1,2] | 15.5[1,2] | 93.1[1,2] | 33.4[1,2] |
| CDME (80 uM) + Menadione | 114.3[1,2] | 13.3[1,2] | 87.0[1,2] | 24.6[1,2] |
| CDME (160 uM) + Menadione | 97.9[2] | 25.7[2] | 105.9[1,2] | 51.7[1,2] |

Statistically significant difference:
[1] $p < 0.05$ compared to vehicle control
Statistically significant difference:
[2] $p < 0.05$ compared to vehicle control + menadione

Example 2

Example 2 evaluated various combinations of 4-alkyl resorcinols and amino acids constituting GSH building blocks for potentiating intracellular GSH production and improved reduction in oxygen species. Results that were obtained are summarized in Tables 2A through 2F.

TABLE 2A

Glutathione Synthesis

| | Sample | Mean (uM glutathione) | % Protection (improvement vs. vehicle control + menadione) |
|---|---|---|---|
| A | Vehicle Control | 2.08 | |
| B | Vehicle Control + Menadione | 0.17 | 0 |
| | Test Samples | | |
| C | HR (10 uM) + Menadione | 0.24 | 4 |
| D | HR (20 uM) + Menadione | 0.28 | 5 |
| E | HR (40 uM) + Menadione | 0.19 | 1 |
| F | HR (60 uM) + Menadione | 0.14 | 0 |
| G | GAP 5 + Menadione | 0.57[1] | 19[1] |
| H | GAP 10 + Menadione | 1.51[1] | 65[1] |
| I | GAP 20 + Menadione | 3.89[1,2] | 187[1,2] |
| 1 | HR (10 uM) + GAP 5 + Menadione | 0.50 | 16 |
| 2 | HR (20 uM) + GAP 5 + Menadione | 0.76[1] | 28 |
| 3 | HR (40 uM) + GAP 5 + Menadione | 0.47 | 15 |
| 4 | HR (60 uM) + GAP 5 + Menadione | 0.16 | 0 |
| 5 | HR (10 uM) + GAP 10 + Menadione | 2.85[1,2,3] | 129[1,2,3] |
| 6 | HR (20 uM) + GAP 10 + Menadione | 2.97[1,2,3] | 135[1,2,3] |
| 7 | HR (40 uM) + GAP 10 + Menadione | 0.82[3] | 31[3] |
| 8 | HR (60 uM) + GAP 10 + Menadione | 0.15 | 0 |

Statistically significant improvement:
[1] $p < 0.05$ compared to vehicle control + menadione
[2] $p < 0.05$ compared to GAP10 + menadione
[3] $p < 0.05$ compared to HR (at equivalent dose) + menadione

TABLE 2B

Glutathione Synthesis

| | Sample | Mean (uM glutathione) | % Protection (improvement vs. vehicle control + menadione) |
|---|---|---|---|
| A | Vehicle Control | 1.87 | |
| B | Vehicle Control + Menadione | 0.01 | 0 |
| | Test Samples | | |
| C | BR (10 uM) + Menadione | 0.10 | 5 |
| D | BR (50 uM) + Menadione | 0.07 | 3 |
| E | BR (100 uM) + Menadione | 0.13 | 6 |
| F | IPR (10 uM) + Menadione | 0.12 | 6 |
| G | IPR (50 uM) + Menadione | 0.12 | 6 |
| H | IPR (100 uM) + Menadione | 0.16 | 8 |
| I | GAP 10 + Menadione | 0.70[1] | 37[1] |
| J | GAP 20 + Menadione | 2.71[1,2] | 144[1,2] |
| 1 | BR (10 uM) + GAP 10 + Menadione | 0.88[1,3] | 46[1,3] |
| 2 | BR (50 uM) + GAP 10 + Menadione | 1.51[1,2,3] | 80[1,2,3] |
| 3 | BR (100 uM) + GAP 10 + Menadione | 0.93[1,3] | 49[1,3] |
| 4 | IPR (10 uM) + GAP 10 + Menadione | 1.02[1,4] | 54[1,4] |

TABLE 2B-continued

Glutathione Synthesis

| | Sample | Mean (uM glutathione) | % Protection (improvement vs. vehicle control + menadione) |
|---|---|---|---|
| 5 | IPR (50 uM) + GAP 10 + Menadione | 1.14[1,2,4] | 60[1,2,4] |
| 6 | IPR (100 uM) + GAP 10 + Menadione | 1.13[1,2,4] | 60[1,2,4] |

Statistically significant improvement:
[1] $p < 0.05$ compared to vehicle control + menadione
[2] $p < 0.05$ compared to GAP10 + menadione
[3] $p < 0.05$ compared to BR (at equivalent dose) + menadione
[4] $p < 0.05$ compared to IPR (at equivalent dose) + menadione

TABLE 2C

Glutathione Synthesis

| | Sample | Mean (uM glutathione) | % Protection (improvement vs. vehicle control + menadione) |
|---|---|---|---|
| A | Vehicle Control | 2.65 | |
| B | Vehicle Control + Menadione | 0.36 | 0 |
| | Test Samples | | |
| C | GAP 10 + Menadione | 2.47[1] | 80[1] |
| D | ER (40 uM) + Menadione | 0.36 | 0 |
| E | ER (50 uM) + Menadione | 0.25 | −4 |
| F | ER (60 uM) + Menadione | 0.34 | −1 |
| 1 | ER (40 uM) + GAP 10 + Menadione | 2.17[1,3] | 68[1,3] |
| 2 | ER (50 uM) + GAP 10 + Menadione | 2.82[1,2,3] | 93[1,2,3] |
| 3 | ER (60 uM) + GAP 10 + Menadione | 3.62[1,2,3] | 123[1,2,3] |

Statistically significant improvement:
[1] $p < 0.05$ compared to vehicle control + menadione
[2] $p < 0.05$ compared to GAP10 + menadione
[3] $p < 0.05$ compared to ER (at equivalent dose) + menadione In Tables 2A-2C, samples marked by alphabetical characters were outside the scope of the invention. Sample I (Table 2A) and Sample J (Table 2B) were positive controls as they employed a high concentration of GAP. Overall, it can be seen from the results in Tables 2A-2C that combination of 4-alkyl resorcinol (HR, BR, IPR, or ER) concentrations with GAP amino acids resulted in synergistic increase in GSH synthesis compared to the GSH synthesis achieved with either resorcinol or GAP alone.

TABLE 2D

Reduction in Oxygen Species

| | Sample | Mean ROS production (% of vehicle control) | % protection (improvement vs vehicle control + menadione) | Cell viability (% of control) | % Protection (improvement vs vehicle control + menadione) |
|---|---|---|---|---|---|
| A | Vehicle Control | 100.0 | | 100.0 | |
| B | Vehicle Control + Menadione | 504.8 | | 54.8 | |
| | Test Samples | | | | |
| C | Menadione + GAP | 171.5[3] | 66.02[3] | 92.7[3] | 69.11[3] |
| D | Menadione + HR (10 uM) | 153.4[3] | 69.6[3] | 65.1[3] | 18.85[3] |
| E | Menadione + HR (20 uM) | 118.7[3] | 76.49[3] | 11.0 | −79.00 |
| 1 | Menadione + HR (10 uM) + GAP | 108.9[1,2,3] | 78.42[1,2,3] | 103.2[2,3] | 88.30[2,3] |
| 2 | Menadione + HR (20 uM) + GAP | 92.5[1,2,3] | 81.68[1,2,3] | 105.2[1,2,3] | 92.02[1,2,3] |

Statistically significant improvement:
[1] $p < 0.05$ compared to menadione + GAP
[2] $p < 0.05$ compared to menadione + HR (at equivalent dose)
[3] $p < 0.05$ compared to vehicle control + menadione

TABLE 2E

Reduction in Oxygen Species

| | Sample | Mean ROS production (% of vehicle control) | % Protection (improvement vs vehicle control + menadione) | cell viability (% of control) | % Protection (improvement vs vehicle control + menadione) |
|---|---|---|---|---|---|
| A | Vehicle control | 100.0 | | 100.0 | |
| B | Menadione + Vehicle Control | 222.8 | | 66.3 | |

TABLE 2E-continued

Reduction in Oxygen Species

| Sample | Mean ROS production (% of vehicle control) | % Protection (improvement vs vehicle control + menadione) | cell viability (% of control) | % Protection (improvement vs vehicle control + menadione) |
|---|---|---|---|---|
| | | Test Samples | | |
| C Menadione + GAP | 136.5[3] | 38.70[3] | 84.5[3] | 27.41[3] |
| D Menadione + BR (20 uM) | 220.7 | 0.95 | 74.1[3] | 11.75[3] |
| 1 Menadione + GAP + BR (20 uM) | 122.2[1,2,3] | 45.20[1,2,3] | 90.9[1,2,3] | 37.07[1,2,3] |

Statistically significant improvement:
[1] $p < 0.05$ compared to menadione + GAP
[2] $p < 0.05$ compared to menadione + BR
[3] $p < 0.05$ compared to vehicle control + menadione

TABLE 2F

Reduction in Oxygen Species

| Sample | Mean ROS production (% of vehicle control) | % protection (improvement vs vehicle control + menadione) | Cell viability (% of control) | % protection (improvement vs vehicle control + menadione) |
|---|---|---|---|---|
| A Vehicle Control | 100.0 | | 100 | |
| B Menadione + Vehicle Control | 301.2 | | 61.7 | |
| | | Test Samples | | |
| C Menadione + GAP | 192.0[3] | 36.26[3] | 76.0[3] | 23.23[3] |
| D Menadione + PER (20 uM) | 321.5 | −6.74 | 62.3 | 1.09 |
| 1 Menadione + GAP + PER (20 uM) | 175.5[1,2,3] | 41.72[1,2,3] | 90.7[1,2,3] | 47.13[1,2,3] |

Statistically significant improvement:
[1] $p < 0.05$ compared to menadione + GAP
[2] $p < 0.05$ compared to menadione + PER
[3] $p < 0.05$ compared to vehicle control + menadione In Tables 2D-F, samples marked by alphabetical characters were outside the scope of the invention. Overall, it can be seen from the results in Tables 2D-F that combination of 4-alkyl resorcinol (HR, BR or PER) with GAP amino acids resulted in a synergistic decrease in ROS production compared to ROS levels achieved with either resorcinol alone or GAP alone.

TABLE 2G

Glutathione Synthesis

| Sample | Mean (uM glutathione) | % Protection (improvement vs vehicle control + menadione) |
|---|---|---|
| A Vehicle Control | 2.76 | |
| B Vehicle Control + Menadione | 0.16 | 0 |
| | Test Samples | |
| C GAP 10 + Menadione | 2.88[1] | 98[1] |
| D PER (10 uM) + Menadione | 0.12 | −2 |
| E PER (20 uM) + Menadione | 0.25 | 3 |
| F PER (50 uM) + Menadione | 0.50 | 12 |
| 1 PER (10 uM) + GAP 10 + Menadione | 2.70 | 92 |
| 2 PER (20 uM) + GAP 10 + Menadione | 1.62 | 53 |
| 3 PER (50 uM) + GAP 10 + Menadione | 1.05 | 32 |

Statistically significant improvement:
[1] $p < 0.05$ compared to vehicle control + menadione

TABLE 2H

Reduction in Oxygen Species

| | Sample | Mean ROS production (% of vehicle control) | Cell viability (% of vehicle of control) |
|---|---|---|---|
| A | Vehicle Control | 100 | 100.0 |
| B | Menadione + Vehicle Control | 311.0 | 35.5 |
| | *Test Samples* | | |
| C | Menadione + GAP | 156.5[1] | 132.61 |
| D | Menadione + ER (10 uM) | 287.5 | 36.6 |
| E | Menadione + ER (20 uM) | 308.3 | 39.8 |
| 1 | Menadione + ER (10 uM) + GAP | 166.1[1] | 126.4[1] |
| 2 | Menadione + ER (20 uM) + GAP | 162.7[1] | 122.3[1] |

Statistically significant improvement:
[1] $p < 0.05$ compared to vehicle control + menadione It can be seen from the results in Table 2G that when PER was tested in Glutathione Assay with GAP amino acids synergistic increase in GSH synthesis was not observed, although the same PER/GAP combination did provide synergistic decrease in in reactive oxygen species—see Table 2F.

On the other hand, results in Table 2H show that when ER was tested in reduction in oxygen species assay, with GAP amino acids synergistic decrease in reactive oxygen species was not observed, although the same ER/GAP combination did provide synergistic increase in GSH synthesis—see Table 2C. Thus, the results in Tables 2G and 2H suggest that the two assays used to evaluate the anti-oxidant activity are not always in agreement, indicating that it may be adviseable to perform both assays, before concluding with certainty the absence of the antioxidant potential.

Comparative Example b 3

Comparative Example 3 investigated glutathione synthesis and reduction in oxygen species of combinations of amino acids and 5-substituted resorcinols (Olivetol, also known as 5-pentylresorcinol), non-resorcinol molecules (3-hydroxytyrosol) or 4-methyl-resorcinol (shorter branch than ethyl), and 4-(cyclohexylmethyl)-resorcinol. The results that were obtained are summarized in Tables 3A through 3D.

TABLE 3A

Glutathione Synthesis

| Sample | Mean (uM glutathione) | % Protection (improvement vs vehicle control + menadione) |
|---|---|---|
| Vehicle Control | 2.76 | |
| Vehicle Control + Menadione | 0.16 | 0 |
| *Test Samples* | | |
| GAP 10 + Menadione | 2.88[1] | 98[1] |
| Olivetol (10 uM) + Menadione | 0.14 | −1 |
| Olivetol (20 uM) + Menadione | 0.13 | −1 |
| Olivetol (50 uM) + Menadione | 0.11 | −2 |
| Olivetol (10 uM) + GAP 10 + Menadione | 1.55 | 50 |
| Olivetol (20 uM) + GAP 10 + Menadione | 1.43 | 46 |
| Olivetol (50 uM) + GAP 10 + Menadione | 1.35 | 43 |
| 3-hydroxytyrosol (10 uM) + Menadione | 0.07 | −3 |
| 3-hydroxytyrosol (20 uM) + Menadione | 0.03 | −5 |
| 3-hydroxytyrosol (50 uM) + Menadione | 0.04 | −4 |
| 3-hydroxytyrosol (10 uM) + GAP 10 + Menadione | 0.33 | 6 |
| 3-hydroxytyrosol (20 uM) + GAP 10 + Menadione | 0.31 | 5 |
| 3-hydroxytyrosol (50 uM) + GAP 10 + Menadione | 0.06 | −3 |
| GAP 20 + Menadione | 6.35[1,2] | 224[1,2] |

Statistically significant improvement:
[1] $p < 0.05$ compared to vehicle control + menadione
[2] $p < 0.05$ compared to GAP10 + menadione

TABLE 3B

Reduction in Reactive oxygen species

| Sample | ROS production (% of vehicle control) | cell viability (% vehicle of control) |
|---|---|---|
| Vehicle Control | 100.0 | 100.0 |
| Menadione + Vehicle Control | 331.1 | 31.8 |
| *Test Samples* | | |
| Menadione + GAP | 145.0[1] | 122.9[1] |
| Menadione + 3-hydroxytyrosol (10 uM) | 241.6 | 16.8 |
| Menadione + 3-hydroxytyrosol (10 uM) + GAP | 150.1[1] | 105.0[1] |
| Menadione + 3-hydroxytyrosol (20 uM) | 229.9[1] | 16.5 |
| Menadione + 3-hydroxytyrosol (20 uM) + GAP | 152.4[1] | 103.9[1] |

Statistically significant improvement:
[1] $p < 0.05$ compared to vehicle control + menadione

TABLE 3C

Reduction in Reactive oxygen species

| Sample | Mean ROS production (% of vehicle control) | Cell viability (% of vehicle control) |
|---|---|---|
| Vehicle Control | 100.0 | 100.0 |
| Menadione + Vehicle Control | 272.8 | 51.2 |
| *Test Samples* | | |
| Menadione + GAP | 157.2[1] | 100.4[1] |
| Menadione + MR (10 uM) | 233.5[1] | 45.3 |
| Menadione + MR (10 uM) + GAP | 170.0[1] | 94.5[1] |

Statistically significant improvement:
[1] $p < 0.05$ compared to vehicle control + menadione

TABLE 3D

| | | Glutathione Synthesis | |
|---|---|---|---|
| | Sample | Mean uM glutathione) | % Protection |
| A | Vehicle Control | 2.693 | |
| B | Vehicle Control + Menadione | 0.193 | 0 |
| | Test Sample | | |
| C | GAP 10 + Menadione | 2.302[1] | 78.3[1] |
| D | 4-CHMR (10 uM) + Menadione | 0.07 | −4.6 |
| E | 4-CHMR (20 uM) + Menadione | 0.026 | −6.2 |
| F | 4-CHMR (50 uM) + Menadione | 0.147 | −1.7 |
| G | 4-CHMR (10 uM) + GAP 10 + Menadione | 3.931[1,3] | 138.8[1,3] |
| H | 4-CHMR (20 uM) + GAP 10 + Menadione | 4.313[1,3] | 153.0[1,3] |
| I | 4-CHMR (50 uM) + GAP 10 + Menadione | 0.147 | −1.7 |
| J | GAP 20 + Menadione | 4.348[1,2] | 154.3[1,2] |

Statistically significant improvement:
[1] $p < 0.05$ compared to vehicle control + menadione
[2] $p < 0.05$ compared to GAP10 + menadione
[3] $p < 0.05$ compared to 4-(cyclohexylmethyl)resorcinol (at equivalent dose) + menadione Collectively, the data in Tables 3A-3D demonstrate that combinations of GAP with resorcinols outside the scope of the invention—i.e. 5-substituted resorcinols (Olivetol, also known as 5-pentylresorcinol), or 4-(cyclohexylmethyl)resorcinol or 4-methylresorcinol—did not result in either synergistic increase in GSH synthesis or in synergistic decrease in reactive oxygen species. Likewise, no synergistic effect was observed with the non-resorcinol molecule 3-OH tyrosol.

Example 4

Example 4 investigated the skin lightening potential of the inventive compositions. The results that were obtained are summarized in Table 4.

TABLE 4

| | Tyrosinase activity inhibition | |
|---|---|---|
| | Sample | Mean of % Inhibition |
| A | Media Control | 0 |
| B | Vehicle Control | 0 |
| | Test Samples | |
| C | GAP | 8[1] |
| D | HR (10 uM) | 71[1] |
| E | HR (5 uM) | 63[1] |
| F | ER (10 uM) | 68[1] |
| G | ER (5 uM) | 67[1] |
| 1 | GAP + HR (10 uM) | 70[1,2] |
| 2 | GAP + HR (5 uM) | 70[1,2,3] |
| 3 | GAP + ER (10 uM) | 76[1,2,4] |
| 4 | GAP + ER (5 uM) | 75[1,2,4] |

Statistically significant improvement:
[1] $p < 0.05$ compared to media and vehicle control
[2] $p < 0.05$ compared to GAP
[3] $p < 0.05$ compared to HR alone (at equivalent doses)
[4] $p < 0.05$ compared to ER alone (at equivalent doses)

In Table 4 samples marked by alphabetical characters were outside the scope of the invention. Numerically marked samples were within the scope of the invention. It can be seen that, overall, combinations of GAP with resorcinol compounds within the scope of the invention resulted in synergistic decrease in tyrosinase activity compared to the tyrosinase activity achieved with either resorcinol or GAP alone.

Example 5

Personal care formulations according to the present invention are illustrated in the Tables below. All numbers in the Tables represent weight % in the composition.

TABLE I

| | Oil-in-water formulations, lotions and creams | | | | |
|---|---|---|---|---|---|
| | OW-1 | OW-2 | OW-3 | OW-4 | OW-5 |
| Water | To 100 | To 100 | To 100 | To 100 | To 100 |
| Glycerine | 0-40 | 1-40 | 1-5 | 1-10 | 1-40 |
| Propylene glycol | 0-5 | | 0-5 | | |
| Butylene glycol | 0-5 | | 0-5 | 0-5 | |
| Carbomer | 0-2 | 0.03-1 | | | |
| Ammonium Acryloyl dimethyl taurate/VP copolymer | 0-1 | | 0.03-1 | | 0.01-1 |
| Styrene/ Acrylates copolymer | 0-1 | | 0.01-1 | | |
| Xanthan Gum | 0-1 | | | | 0.01-1 |
| EDTA | 0.01-0.01 | 0.01-0.01 | 0.01-1 | 0.01-1 | 0.01-1 |
| Preservative | 0.02-2 | 0.02-2 | 0.02-2 | 0.02-2 | 0.02-2 |
| Titanium oxide | 0-10 | 0.01-10 | 0.01-10 | 0.01-10 | 0.01-10 |
| Colorant/ Pigment | 0-5 | 0-5 | 0-5 | 0-5 | 0-5 |
| Triethanol amine/ Sodium Hydroxide/ potassium Hydroxide | 0-3 | 0.01-3 | 0.01-3 | 0.01-3 | 0.01-3 |
| Stearic acid | 0-5 | 0.01-5 | 0.01-5 | 0.01-5 | 0.01-5 |
| Isopropyl Myristate | 0-10 | 0.01-10 | | | |
| Capric/ Caprylic Triglyceride | 0-10 | 0.01-10 | | | |
| C12-C15 alkyl benzoate | 0-10 | | | | 0.01-10 |
| Mineral oil | 0-10 | | | 0.01-10 | |
| Glyceryl stearate | 0-5 | 0.01-5 | | | |
| Steareth-2 | 0-5 | | 0.01-5 | | 0.01-5 |
| Steareth-21 | 0-5 | | 0.01-5 | | |
| Peg100 Stearate | 0-5 | | | 0.01-2 | 0.01-5 |
| Potassium Cetyl Phosphate | 0-5 | | | 0.01-2 | |
| Tween20 | 0-5 | | | | 0.01-5 |
| Cetyl alcohol | 0-4 | 0.01-4 | | 0.01-4 | |
| Dicaprylyl carbonate | 0-5 | | 0.01-5 | | |
| Ethyl hexyl methoxy-cinnamate | 0-6 | 0.01-6 | | | |
| Butyl Methoxy-dibenzoyl-methane | 0-3 | 0.01-3 | | 0.01-3 | 0.01-3 |
| Ensulizole | 0-4 | | | | 0.01-4 |
| Octinoxate | 0-7.5 | | | | |
| Octisalate | 0-5 | | | 0.01-5 | 0.01-5 |
| Octocrylene | 0-10 | | | 0.01-10 | 0.01-10 |

TABLE I-continued

Oil-in-water formulations, lotions and creams

| | OW-1 | OW-2 | OW-3 | OW-4 | OW-5 |
|---|---|---|---|---|---|
| Homosalate | 0-10 | | | 0.01-10 | |
| Dimethicone | 0-10 | 0.01-10 | 0.01-10 | | |
| Cyclomethicone | 0-15 | | 0.01-15 | | |
| Niacinamide | 0-5 | 0-5 | 0-5 | 0-5 | 0-5 |
| Fragrance | 0-2 | 0-2 | 0-2 | 0-2 | 0-2 |
| Glutamine/Sodium PCA | 0.01-10 | 0.01-10 | 0.01-10 | 0.01-10 | |
| Glycine | | 0.01-10 | 0.01-10 | 0.01-10 | 0.01-10 |
| Cystine | 0.001-2 | 0.001-2 | 0.001-2 | 0.001-2 | 0.001-2 |
| 4-hexyl-resorcinol | 0.001-3 | | | | 0.001-3 |
| 4-ethyl-resorcinol | | 0.001-3 | | | 0.001-3 |
| 4-butyl-resorcinol | | | 0.001-3 | | |
| 4-(1-phenylethyl) resorcinol | | | | 0.001-3 | |

TABLE II

Water-in-oil topical lotions or creams

| | WO-1 | WO-2 | WO-3 | WO-4 |
|---|---|---|---|---|
| Water | To 100 | To 100 | To 100 | To 100 |
| Glycerine | 0-70 | 1-70 | 1-70 | |
| Propylene glycol | 0-5 | | | 0.01-5 |
| Butylene glycol | 0-5 | | 0.01-5 | 0.01-5 |
| Disteardimonium Hectorite | 0.01-1 | 0.01-1 | | |
| EDTA | 0.01-.01 | 0.01-1 | 0.01-1 | 0.01-1 |
| Preservative | 0.02-2 | 0.02-2 | 0.02-2 | 0.02-2 |
| TiO2 | 0-10 | 0.01-10 | 0.01-10 | 0.01-10 |
| Colorant/pigment | 0-5 | 0-5 | 0-5 | 0-5 |
| TEA/Sodium Hydroxide/potassium Hydroxide | 0-3 | 0.01-3 | 0.01-3 | 0.01-3 |
| Stearic acid | 0-5 | 0.01-5 | | |
| Isopropyl Myristate | 0-10 | | | |
| Capric/Caprylic Triglyceride | 0-10 | | 0.01-10 | |
| C12-C15 alkyl benzoate | 0-10 | | | 0.01-10 |
| Mineral oil | 0-10 | | | |
| Glyceryl stearate | 0-5 | | | |
| Dimethicone copolyol | 0-5 | 0.01-5 | 0.01-5 | |
| Cetyl PEG/PPG-10/1 Dimethicone | 0-5 | | | 0.01-5 |
| Steareth-2 | 0-2 | | | |
| Sucrose Distearate | 0-2 | 0.01-2 | | |
| Cetyl alcohol | 0-2 | 0.01-2 | 0.01-2 | |
| Ethyl hexyl methoxycinnamate | 0-6 | 0.01-6 | | |
| Butyl Methoxy-dibenzoylmethane | 0-3 | 0.01-3 | 0.01-3 | 0.01-3 |
| Ensulizole | 0-4 | | 0.01-4 | |
| Octinoxate | 0-7.5 | | | |
| Octisalate | 0-5 | | 0.01-5 | 0.01-5 |
| Octocrylene | 0-10 | | 0.01-10 | 0.01-10 |
| Homosalate | 0-10 | | | 0.01-10 |
| Dimethicone | 0-10 | | 0.01-10 | 0.01-10 |
| Cyclomethicone | 0-40 | 0.01-40 | | 0.01-10 |
| Caprylyl methicone | 0-10 | 0.01-10 | | 0.01-10 |
| Dimethicone crosspolymer | 0-90 | 0.01-90 | 0.01-90 | |
| C30-C45 alkyl cetearyl dimethicone crosspolymer | | | | 0.01-90 |
| Glycolic acid | 0-10 | 0.01-10 | | |
| KCl | 0-5 | 0.01-5 | 0.01-5 | 0.01-5 |
| Iacinamide | 0-5 | 0.01-5 | 0.01-5 | 0.01-5 |
| Fragrance | 0-2 | 0-2 | 0-2 | 0-2 |

TABLE II-continued

Water-in-oil topical lotions or creams

| | WO-1 | WO-2 | WO-3 | WO-4 |
|---|---|---|---|---|
| Glutamine/Sodium PCA | 0.01-10 | 0.01-10 | 0.01-10 | 0.01-10 |
| Glycine | | 0.01-10 | 0.01-10 | 0.01-10 |
| Cystine | 0.001-2 | 0.001-2 | 0.001-2 | 0.001-2 |
| 4-hexylresorcinol | 0.001-3 | | | |
| 4-ethylresorcinol | | 0.001-3 | | |
| 4-butylresorcinol | | | 0.001-3 | |
| 4-(1-phenylethyl) resorcinol | | | | 0.001-3 |

TABLE III

Vanishing Creams

| | VC-1 | VC-2 | VC-3 | VC-4 |
|---|---|---|---|---|
| Water | To 100 | To 100 | To 100 | To 100 |
| Glycerine | 0-5 | 0.01-5 | 0.01-5 | |
| EDTA | 0.01-.01 | 0.01-.01 | 0.01-.01 | 0.01-.01 |
| Preservative | 0.02-2 | 0.02-2 | 0.02-2 | 0.02-2 |
| TiO2 | 0.01-10 | 0.01-10 | 0.01-10 | 0.01-10 |
| Colorant/pigment | 0-5 | 0.01-5 | 0.01-5 | |
| TEA/Sodium Hydroxide/potassium Hydroxide | 0-3 | 0.01-3 | 0.01-3 | 0.01-3 |
| Stearic acid | 0-30 | 0.01-30 | 0.01-30 | 0.01-30 |
| Isopropyl Myristate | 0-5 | 0.01-10 | 0.01-10 | |
| C12-C15 alkyl benzoate | 0-5 | | | 0.01-10 |
| Brij 35 | 0-5 | 0.01-5 | | |
| Tween40 | 0-5 | | | 0.01-5 |
| Cetyl alcohol | 0-2 | 0.01-2 | 0.01-2 | |
| Ethyl hexyl methoxycinnamate | 0-6 | 0.01-6 | 0.01-6 | |
| Butyl Methoxy-dibenzoylmethane | 0-3 | 0.01-3 | 0.01-3 | 0.01-3 |
| Ensulizole | 0-4 | | | 0.01-4 |
| Octisalate | 0-5 | | | 0.01-5 |
| Octocrylene | 0-10 | | 0.01-10 | 0.01-10 |
| Dimethicone | 0-5 | 0.01-5 | | |
| Cyclomethicone | 0-5 | | | 0.01-5 |
| Dimethicone crosspolymer | 0-4 | | | 0.01-4 |
| Niacinamide | 0-5 | 0.01-5 | 0.01-5 | 0.01-5 |
| Hydroxystearic acid | 0-5 | 0.01-5 | 0.01-5 | 0.01-5 |
| Fragrance | 0-2 | 0-2 | 0-2 | 0-2 |
| Glutamine/Sodium PCA | 0.01-10 | 0.01-10 | 0.01-10 | 0.01-10 |
| Glycine | | 0.01-10 | 0.01-10 | 0.01-10 |
| Cystine | 0.001-2 | 0.001-2 | 0.001-2 | 0.001-2 |
| 4-hexylresorcinol | 0.001-3 | | | |
| 4-ethylresorcinol | | 0.001-3 | | |
| 4-butylresorcinol | | | 0.001-3 | |
| 4-(1-phenylethyl) resorcinol | | | | 0.001-3 |

The invention claimed is:

1. A personal care composition comprising:
   a. glutathione precursor comprising, by weight of the composition:
      i. from about 0.001% to about 2% of cystine;
      ii. optionally, from about 0.01 to about 10% of glycine;
      iii. from about 0.01 to about 10% of pyroglutamic acid or a salt or ester thereof; and
      iv. from about 0.001 to about 3% of a resorcinol selected from 4-hexylresorcinol, 4-ethylresorcinol, and 4-isopropylresorcinol;
   b. from about 0.005% to about 2% of a retinoid; and
   c. a cosmetically acceptable carrier;
   wherein the pH of the composition is in the range of from about 3.5 to about 8.5, and
   wherein the composition is in the form of a water-in-oil emulsion comprising cystine in an aqueous phase, wherein 90% of water droplets have a diameter within the size range of from 100 nm to 20 microns.

2. The composition of claim 1, wherein the retinoid is selected from retinol, retinol esters, retinal, retinoic acid and derivatives and mixtures thereof.

3. The composition of claim 2, wherein retinol esters are selected from retinyl palmitate, retinyl acetate, retinyl propionate and mixtures thereof.

4. The composition of claim 1, wherein the composition is a leave-on non-solid skin cosmetic composition.

5. The composition of claim 1, wherein the composition further comprises a nicotinamide compound.

6. A method for improving the appearance of skin comprising applying to the skin the composition of claim 1.

7. A personal care composition comprising:
 a. glutathione precursor comprising, by weight of the composition:
  i. from about 0.0001% to about 2% of cystine;
  ii. from about 0.01% to about 10% of glycine; and
  iii. from about 0.001% to about 3% of 4-hexylresorcinol;
 b. from about 0.0001% to about 10% of at least one vitamin; and
 c. a cosmetically acceptable carrier;
wherein the pH of the composition is in the range of from about 3.5 to about 8.5; and
wherein the composition is in the form of a water-in-oil emulsion comprising cystine in an aqueous phase, wherein 90% of water droplets have a diameter within the size range of from 100 nm to 20 microns.

8. The composition according to claim 7, wherein the vitamin is selected from Vitamin A, Vitamin B2, Vitamin B3, Vitamin B6, Vitamin B12, Vitamin C, Vitamin D, Vitamin E, Vitamin K and derivatives and mixtures thereof.

9. The composition of claim 7, wherein the composition is a leave-on non-solid skin cosmetic composition.

10. The composition of claim 7, wherein the composition further comprises a nicotinamide compound.

11. A method for improving the appearance of skin comprising applying to the skin the composition of claim 7.

* * * * *